United States Patent
Karlstrom et al.

(10) Patent No.: US 9,000,184 B2
(45) Date of Patent: *Apr. 7, 2015

(54) CYCLOHEXANE-1,2'-NAPHTHALENE-1',2"-IMIDAZOL COMPOUNDS AND THEIR USE AS BACE INHIBITORS

(71) Applicant: AstraZeneca AB, Sodertalje (SE)

(72) Inventors: Sofia Karlstrom, Cheshire (GB); Lars Sandberg, Cheshire (GB); Peter Soderman, Cheshire (GB); Karin Kolmodin, Cheshire (GB); Liselotte Ohberg, Cheshire (GB)

(73) Assignee: AstraZeneca AB, Sodertalje (SE)

(*) Notice: Subject to any disclaimer, the term of this patent is extended or adjusted under 35 U.S.C. 154(b) by 0 days.

This patent is subject to a terminal disclaimer.

(21) Appl. No.: 13/916,731

(22) Filed: Jun. 13, 2013

(65) Prior Publication Data

US 2013/0345248 A1 Dec. 26, 2013

Related U.S. Application Data

(60) Provisional application No. 61/661,922, filed on Jun. 20, 2012.

(51) Int. Cl.
| | | |
|---|---|---|
| C07D 235/02 | (2006.01) | |
| C07D 401/02 | (2006.01) | |
| C07D 491/107 | (2006.01) | |
| A61K 31/4184 | (2006.01) | |
| A61K 31/4439 | (2006.01) | |
| A61K 45/06 | (2006.01) | |
| C07D 401/04 | (2006.01) | |

(52) U.S. Cl.
CPC ............ *C07D 235/02* (2013.01); *C07D 401/02* (2013.01); *A61K 31/4184* (2013.01); *A61K 31/4439* (2013.01); *A61K 45/06* (2013.01); *C07D 401/04* (2013.01); *C07D 491/107* (2013.01)

(58) Field of Classification Search
USPC ..................................................... 548/301.1
See application file for complete search history.

(56) References Cited

U.S. PATENT DOCUMENTS

| | | | | |
|---|---|---|---|---|
| 8,415,483 | B2 * | 4/2013 | Csjernyik et al. .......... | 548/301.1 |
| 8,865,911 | B2 * | 10/2014 | Csjernyik et al. .......... | 548/301.1 |
| 2013/0210837 | A1 * | 8/2013 | Csjernyik et al. ......... | 514/255.05 |
| 2013/0345246 | A1 | 12/2013 | Karlstrom et al. | |
| 2013/0345247 | A1 | 12/2013 | Karlstrom et al. | |
| 2013/0345272 | A1 | 12/2013 | Karlstrom et al. | |
| 2014/0031379 | A1 | 1/2014 | Bohlin et al. | |

FOREIGN PATENT DOCUMENTS

| | | |
|---|---|---|
| WO | WO2005094822 | 10/2005 |
| WO | WO2006138264 | 12/2006 |
| WO | WO2007076247 | 7/2007 |
| WO | WO2007100536 | 9/2007 |
| WO | WO2008076043 | 6/2008 |
| WO | WO2009100169 | 8/2009 |
| WO | WO2010013794 | 2/2010 |
| WO | WO2010021680 | 2/2010 |
| WO | WO2010030954 | 3/2010 |
| WO | WO2010105179 | 9/2010 |
| WO | WO2011002407 | 1/2011 |
| WO | WO2011002408 | 1/2011 |
| WO | WO2011106414 | 9/2011 |
| WO | WO2011123674 | 10/2011 |
| WO | WO2011130741 | 10/2011 |
| WO | WO2012019056 | 2/2012 |
| WO | WO2012040641 | 3/2012 |
| WO | WO2012071458 | 5/2012 |
| WO | WO2012087237 | 6/2012 |

OTHER PUBLICATIONS

Thompson et al., Current Medicinal Chemistry, Oct. 2002, 9(19), pp. 1751-1762.*
Evin et al., "BACE inhibitors as potential therapeutics for Alzheimer's disease," Recent Patents on CNS Drug Discovery, Bentham Science Publishers Ltd, NL, vol. 2, No. 3, Nov. 1, 2007, pp. 188-199.
Hong et al., "Structure of the Protease Domain of Memapsin 2 (β-Secretase) Complexed with Inhibitor," Science 2000, 290, 5489, pp. 150-153.
John et al, "Human β-Secretase (BACE) and BACE Inhibitors," Journal of Medicinal Chemistry, 2003, 46, pp. 4625-4630.
Roberds et al, "BACE knockout mice are healthy despite lacking the primary β-secretase activity in brain: implications for Alzheimer's disease therapeutics," Human Molecular Genetics, 2001, 10, pp. 1317-1324.
Sinha et al, "Purification and cloning of amyloid precursor protein β-secretase from human brain," Nature, 1999, 402, pp. 537-540.

* cited by examiner

*Primary Examiner* — Laura L. Stockton
(74) *Attorney, Agent, or Firm* — Ropes & Gray LLP

(57) ABSTRACT

Cyclohexane-1,2'-naphthalene-1',2"-imidazole compounds, therapeutically acceptable salts thereof, processes for preparation thereof, therapeutic uses of such compounds for treating Aβ-related pathologies such as Down's syndrome, β-amyloid angiopathy, Alzheimer's disease, memory loss, attention deficit symptoms associated with Alzheimer's disease, neurodegeneration associated with diseases such as Alzheimer's disease or dementia including dementia of mixed vascular and degenerative origin, pre-senile dementia, senile dementia and dementia associated with Parkinson's disease, progressive supranuclear palsy or cortical basal degeneration, methods of therapy using such compounds, and pharmaceutical compositions containing such compounds.

18 Claims, No Drawings

US 9,000,184 B2

CYCLOHEXANE-1,2'-NAPHTHALENE-1',2''-IMIDAZOL COMPOUNDS AND THEIR USE AS BACE INHIBITORS

CROSS-REFERENCE TO RELATED APPLICATIONS

This application claims the benefit under 35 U.S.C. §119 (e) to U.S. Application No. 61/661,922 filed on Jun. 20, 2012, which is incorporated herein by reference.

FIELD OF THE INVENTION

The present invention relates to cyclohexane-1,2'-naphthalene-1',2''-imidazole compounds and therapeutically acceptable salts thereof, their pharmaceutical compositions, processes for making them and their use as medicaments for treatment and/or prevention of various diseases. In particular the invention relates to compounds, which are inhibitors of β-secretase and hence inhibit the formation of amyloid β (Aβ) peptides and will be used for treatment and/or prevention of Aβ-related pathologies such as Alzheimer's disease, Down's syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer's disease, memory loss, attention deficit symptoms associated with Alzheimer's disease, neurodegeneration associated with diseases such as Alzheimer's disease or dementia including dementia of mixed vascular and degenerative origin, pre-senile dementia, senile dementia and dementia associated with Parkinson's disease, progressive supranuclear palsy or cortical basal degeneration.

BACKGROUND

The prime neuropathological event distinguishing Alzheimer's disease (AD) is deposition of the 40-42 residue amyloid β-peptide (Aβ) in brain parenchyma and cerebral vessels. A large body of genetic, biochemical and in vivo data support a pivotal role for Aβ in the pathological cascade that eventually leads to AD. Patients usually present early symptoms (commonly memory loss) in their sixth or seventh decades of life. The disease progresses with increasing dementia and elevated deposition of Aβ. In parallel, a hyperphosphorylated form of the microtubule-associated protein tau accumulates within neurons, leading to a plethora of deleterious effects on neuronal function. The prevailing working hypothesis regarding the temporal relationship between Aβ and tau pathologies states that Aβ deposition precedes tau aggregation in humans and animal models of the disease. Within this context, it is worth noting that the exact molecular nature of Aβ, mediating this pathological function is presently an issue under intense study. Most likely, there is a continuum of toxic species ranging from lower order Aβ oligomers to supramolecular assemblies such as Aβ fibrils.

The Aβ peptide is an integral fragment of the Type I protein APP (Aβ amyloid precursor protein), a protein ubiquitously expressed in human tissues. Since soluble Aβ can be found in both plasma and cerebrospinal fluid (CSF), and in the medium from cultured cells, APP has to undergo proteolysis. There are three main cleavages of APP that are relevant to the pathobiology of AD, the so-called α-, β-, and γ-cleavages. The α-cleavage, which occurs roughly in the middle of the Aβ domain in APP is executed by the metalloproteases ADAM10 or ADAM17 (the latter also known as TACE). The β-cleavage, occurring at the N terminus of Aβ, is generated by the transmembrane aspartyl protease Beta site APP Cleaving Enzyme1 (BACE1). The γ-cleavage, generating the Aβ C termini and subsequent release of the peptide, is effected by a multi-subunit aspartyl protease named γ-secretase. ADAM10/17 cleavage followed by γ-secretase cleavage results in the release of the soluble p3 peptide, an N-terminally truncated Aβ fragment that fails to form amyloid deposits in humans. This proteolytic route is commonly referred to as the non-amyloidogenic pathway. Consecutive cleavages by BACE1 and γ-secretase generates the intact Aβ peptide, hence this processing scheme has been termed the amyloidogenic pathway. With this knowledge at hand, it is possible to envision two possible avenues of lowering Aβ production: stimulating non-amyloidogenic processing, or inhibit or modulate amyloidogenic processing. This application focuses on the latter strategy, inhibition or modulation of amyloidogenic processing.

Amyloidogenic plaques and vascular amyloid angiopathy also characterize the brains of patients with Trisomy 21 (Down's Syndrome), Hereditary Cerebral Hemorrhage with Amyloidosis of the Dutch-type (HCHWA-D), and other neurodegenerative disorders. Neurofibrillary tangles also occur in other neurodegenerative disorders including dementia-inducing disorders (Varghese, J., et al, Journal of Medicinal Chemistry, 2003, 46, 4625-4630). β-amyloid deposits are predominately an aggregate of Aβ peptide, which in turn is a product of the proteolysis of amyloid precursor protein (APP). More specifically, Aβ peptide results from the cleavage of APP at the C-terminus by one or more γ-secretases, and at the N-terminus by β-secretase enzyme (BACE), also known as aspartyl protease or Asp2 or Beta site APP Cleaving Enzyme (BACE), as part of the β-amyloidogenic pathway.

BACE activity is correlated directly to the generation of Aβ peptide from APP (Sinha, et al, Nature, 1999, 402, 537-540), and studies increasingly indicate that the inhibition of BACE inhibits the production of Aβ peptide (Roberds, S. L., et al, Human Molecular Genetics, 2001, 10, 1317-1324). BACE is a membrane bound type 1 protein that is synthesized as a partially active proenzyme, and is abundantly expressed in brain tissue. It is thought to represent the major β-secretase activity, and is considered to be the rate-limiting step in the production of amyloid-β-peptide (Aβ).

Drugs that reduce or block BACE activity should therefore reduce Aβ levels and levels of fragments of Aβ in the brain, or elsewhere where Aβ or fragments thereof deposit, and thus slow the formation of amyloid plaques and the progression of AD or other maladies involving deposition of Aβ or fragments thereof. BACE is therefore an important candidate for the development of drugs as a treatment and/or prophylaxis of Aβ-related pathologies such as Down's syndrome, β-amyloid angiopathy such as but not limited to cerebral amyloid angiopathy or hereditary cerebral hemorrhage, disorders associated with cognitive impairment such as but not limited to MCI ("mild cognitive impairment"), Alzheimer's Disease, memory loss, attention deficit symptoms associated with Alzheimer's disease, neurodegeneration associated with diseases such as Alzheimer's disease or dementia including dementia of mixed vascular and degenerative origin, pre-senile dementia, senile dementia and dementia associated with Parkinson's disease, progressive supranuclear palsy or cortical basal degeneration.

It would therefore be useful to inhibit the deposition of Aβ and portions thereof by inhibiting BACE through inhibitors such as the compounds provided herein.

The therapeutic potential of inhibiting the deposition of Aβ has motivated many groups to isolate and characterize secretase enzymes and to identify their potential inhibitors.

DISCLOSURE OF THE INVENTION

The present invention is directed to compounds according to formula (I):

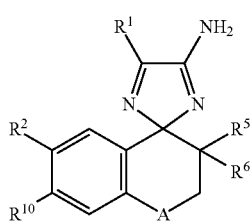

wherein
A is —O— or —CH$_2$—;
R$^1$ is C$_{1-6}$alkyl or C$_{1-6}$haloalkyl;
R$^2$ is hydrogen, C$_{0-6}$alkylaryl, C$_{0-6}$alkylheteroaryl, C$_{2-6}$alkynyl, C$_{2-6}$alkenyl, C$_{1-6}$alkyl, halogen, cyano, C$_{1-6}$haloalkyl, NHC(O)R$^9$ or OR$^8$, wherein said C$_{0-6}$alkylaryl, C$_{0-6}$alkylheteroaryl, C$_{2-6}$alkynyl, C$_{2-6}$alkenyl, C$_{1-6}$alkyl or C$_{1-6}$haloalkyl is optionally substituted with one to three R$^7$;
R$^5$ and R$^6$ are independently hydrogen, heterocyclyl, C$_{3-6}$cycloalkyl, aryl, heteroaryl or C$_{1-6}$alkyl, wherein said heterocyclyl, C$_{3-6}$cycloalkyl, aryl, heteroaryl or C$_{1-6}$alkyl is optionally substituted with one or two substituents independently selected from halogen, C$_{1-6}$alkyl, C$_{1-6}$haloalkyl, cyano or OR$^8$;
or R$^5$ and R$^6$ together with the carbon to which they are attached, form a ring B, which is a 3-14 membered cycloalkyl or heterocyclyl monocyclic ring, or a 9-14 membered bicyclic cycloalkyl or heterocyclyl ring; and wherein ring B is optionally substituted by one or two substituents independently selected from oxo, halogen, C$_{1-6}$alkyl, C$_{1-6}$haloalkyl, cyano, or OR$^8$; and ring B is optionally fused with an aryl or heteroaryl to form a bi- or polycyclic system;
R$^7$ is independently C$_{1-6}$alkyl, halogen, cyano, C$_{0-6}$alkylC$_{3-6}$cycloalkyl, C$_{1-6}$haloalkyl, OC$_{1-6}$alkyl, OC$_{1-6}$haloalkyl, C$_{2-6}$alkynyl or C$_{2-6}$alkenyl, wherein said C$_{1-6}$alkyl, C$_{0-6}$alkylC$_{3-6}$cycloalkyl, C$_{1-6}$haloalkyl, OC$_{1-6}$alkyl, OC$_{1-6}$haloalkyl, C$_{2-6}$alkynyl or C$_{2-6}$alkenyl is optionally substituted with 1-3 substituents independently selected from halogen, cyano, C$_{1-6}$alkyl, C$_{3-6}$cycloalkyl, C$_{3-6}$halocycloalkyl, C$_{1-6}$haloalkyl, OC$_{1-6}$alkyl and OC$_{1-6}$haloalkyl;
R$^8$ is independently hydrogen, C$_{1-6}$alkyl, C$_{2-6}$alkynyl, C$_{1-6}$haloalkyl, aryl or heteroaryl, wherein said C$_{1-6}$alkyl, C$_{1-6}$haloalkyl, aryl or heteroaryl is optionally substituted with a group selected from halogen, cyano, C$_{3-6}$cycloalkyl, C$_{3-6}$halocycloalkyl, OC$_{1-6}$alkyl and C$_{1-6}$alkyl;
R$^9$ is a heteroaryl, wherein said heteroaryl is optionally substituted with halogen, cyano, OR$^8$, C$_{1-6}$haloalkyl or C$_{1-6}$alkyl;
R$^{10}$ is hydrogen, halogen or methyl;
as a free base or a pharmaceutically acceptable salt thereof.

In one embodiment of the present invention, A is —CH$_2$—.
In one embodiment of the present invention, R$^1$ is C$_{1-3}$alkyl. In another embodiment of the invention, R$^1$ is methyl or ethyl. In yet another embodiment, R$^1$ is methyl.
In one embodiment of the present invention, R$^2$ is aryl, heteroaryl, C$_{2-6}$alkynyl, halogen, NHC(O)R$^9$ or OR$^8$, wherein said aryl, heteroaryl or C$_{2-6}$alkynyl is optionally substituted with one to three R$^7$. In another embodiment of the invention, R$^2$ is aryl, heteroaryl, C$_{2-6}$alkynyl or OR$^8$, wherein said aryl, heteroaryl or C$_{2-6}$alkynyl is optionally substituted with one to three R$^7$.
In one embodiment of the present invention, R$^5$ and R$^6$ are independently hydrogen, C$_{3-6}$cycloalkyl or heterocyclyl wherein said C$_{3-6}$cycloalkyl or heterocyclyl is optionally substituted with one or two substituents independently selected from C$_{1-6}$alkyl or OR$^8$.
In one embodiment of the present invention, R$^5$ and R$^6$ together with the carbon to which they are attached, form a ring B, which is a 3-14 membered cycloalkyl or heterocyclyl monocyclic ring, or a 9-14 membered bicyclic cycloalkyl or heterocyclyl ring; and wherein ring B is optionally substituted by one or two substituents independently selected from oxo, halogen, C$_{1-6}$alkyl or OR$^8$; and ring B is optionally fused with an aryl or heteroaryl to form a bi- or polycyclic system.
In another embodiment of the invention, R$^5$ and R$^6$ together with the carbon to which they are attached, form a ring B, which is a 3-14 membered cycloalkyl monocyclic ring; and wherein ring B is optionally substituted by one or two substituents independently selected from oxo, halogen, C$_{1-6}$alkyl or OR$^8$. In yet another embodiment, R$^5$ and R$^6$ together with the carbon to which they are attached form a cyclohexyl ring, which is substituted with OR$^8$.
In one embodiment of the present invention, R$^7$ is independently C$_{1-6}$alkyl, halogen, cyano, C$_{0-6}$alkylC$_{3-6}$cycloalkyl, C$_{1-6}$haloalkyl, OC$_{1-6}$alkyl, OC$_{1-6}$haloalkyl, or C$_{2-6}$alkynyl, wherein said C$_{1-6}$alkyl, C$_{0-6}$alkylC$_{3-6}$cycloalkyl, C$_{1-6}$haloalkyl, OC$_{1-6}$alkyl, or C$_{2-6}$alkynyl is optionally substituted with 1-3 substituents independently selected from halogen, cyano, C$_{1-6}$alkyl, C$_{3-6}$cycloalkyl, C$_{3-6}$halocycloalkyl, C$_{1-6}$haloalkyl, OC$_{1-6}$alkyl and OC$_{1-6}$haloalkyl. In another embodiment of the invention, R$^7$ is halogen, cyano, C$_{0-6}$alkylC$_{3-6}$cycloalkyl, C$_{1-6}$haloalkyl, OC$_{1-6}$alkyl or C$_{2-6}$alkynyl, wherein said C$_{0-6}$alkylC$_{3-6}$cycloalkyl, C$_{1-6}$haloalkyl, OC$_{1-6}$alkyl, or C$_{2-6}$alkynyl is optionally substituted with 1-3 substituents independently selected from C$_{1-6}$alkyl, C$_{3-6}$cycloalkyl, C$_{3-6}$halocycloalkyl and C$_{1-6}$haloalkyl.
In one embodiment of the present invention, R$^8$ is independently hydrogen, C$_{1-6}$alkyl, or C$_{1-6}$haloalkyl. In another embodiment of the invention, R$^8$ is independently C$_{1-6}$alkyl or C$_{1-6}$haloalkyl.
In one embodiment of the present invention, R$^9$ is heteroaryl; wherein said heteroaryl is optionally substituted with halogen, cyano, OR$^8$, C$_{1-6}$haloalkyl or C$_{1-6}$alkyl.
In one embodiment of the present invention, R$^{10}$ is hydrogen. In one embodiment of the present invention, R$^{10}$ is halogen. In one embodiment of the present invention, R$^{10}$ is methyl.

In one embodiment of the present invention,
A is —O— or —CH$_2$—;
R$^1$ is C$_{1-6}$alkyl;
R$^2$ is aryl, heteroaryl, C$_{2-6}$alkynyl, halogen, NHC(O)R$^9$ or OR$^8$; wherein said aryl, heteroaryl or C$_{2-6}$alkynyl is optionally substituted with one to three R$^7$;
R$^5$ and R$^6$ are independently hydrogen, C$_{3-6}$cycloalkyl or heterocyclyl, wherein said C$_{3-6}$cycloalkyl or heterocyclyl, is optionally substituted with one or two substituents independently selected from halogen, C$_{1-6}$alkyl, C$_{1-6}$haloalkyl, cyano or OR$^8$;
or R$^5$ and R$^6$ together with the carbon to which they are attached, form a ring B, which is a 3-14 membered cycloalkyl or heterocyclyl monocyclic ring; and wherein ring B is optionally substituted by one or two substituents independently selected from oxo, halogen, C$_{1-6}$alkyl or OR$^8$;
R$^7$ is independently C$_{1-6}$alkyl, halogen, cyano, C$_{0-6}$alkylC$_{3-6}$cycloalkyl, C$_{1-6}$haloalkyl, OC$_{1-6}$alkyl, OC$_{1-6}$haloalkyl, or C$_{2-6}$alkynyl, wherein said C$_{1-6}$alkyl, $C_{0-6}$alkyl$C_{3-6}$cycloalkyl, $C_{1-6}$haloalkyl, $OC_{1-6}$alkyl or $C_{2-6}$alkynyl is optionally substituted with 1-3 substituents independently selected from halogen, cyano, $C_{1-6}$alkyl, $C_{3-6}$cycloalkyl, $C_{3-6}$halocycloalkyl, $C_{1-6}$haloalkyl, $OC_{1-6}$alkyl and $OC_{1-6}$haloalkyl;

$R^8$ is independently hydrogen, $C_{1-6}$alkyl or $C_{1-6}$haloalkyl; wherein said $C_{1-6}$alkyl or $C_{1-6}$haloalkyl is optionally substituted with a group selected from halogen, cyano, $C_{3-6}$cycloalkyl, $C_{3-6}$halocycloalkyl, $OC_{1-6}$ alkyl or $C_{1-6}$ alkyl;

$R^9$ is heteroaryl, wherein said heteroaryl is optionally substituted with halogen, cyano, $OR^8$, $C_{1-6}$haloalkyl or $C_{1-6}$alkyl; and $R^{10}$ is hydrogen.

In one embodiment of the present invention,

A is —O— or —CH$_2$—;

$R^1$ is $C_{1-3}$alkyl;

$R^2$ is aryl, heteroaryl, $C_{2-6}$alkynyl, halogen, NHC(O)$R^9$ or $OR^8$, wherein said aryl, heteroaryl or $C_{2-6}$alkynyl is optionally substituted with one to three $R^7$;

$R^5$ and $R^6$ are independently hydrogen, $C_{3-6}$cycloalkyl or heterocyclyl, wherein said $C_{3-6}$cycloalkyl or heterocyclyl is optionally substituted with two substituents independently selected from $C_{1-6}$alkyl or $OR^8$;

or $R^5$ and $R^6$ together with the carbon to which they are attached, form a ring B, which is a 3-14 membered cycloalkyl or heterocyclyl monocyclic ring; and wherein ring B is optionally substituted by one or two substituents independently selected from oxo, halogen, $C_{1-6}$alkyl or $OR^8$;

$R^7$ is independently $C_{1-6}$alkyl, halogen, cyano, $C_{0-6}$alkyl$C_{3-6}$cycloalkyl, $C_{1-6}$haloalkyl, $OC_{1-6}$alkyl, $OC_{1-6}$haloalkyl, or $C_{2-6}$alkynyl, wherein said $C_{1-6}$alkyl, $C_{0-6}$alkyl$C_{3-6}$cycloalkyl, $C_{1-6}$haloalkyl, $OC_{1-6}$alkyl or $C_{2-6}$alkynyl, is optionally substituted with 1-3 substituents independently selected from halogen, cyano, $C_{3-6}$cycloalkyl, $C_{3-6}$halocycloalkyl, $C_{1-6}$alkyl, $C_{1-6}$haloalkyl, $OC_{1-6}$alkyl and $OC_{1-6}$haloalkyl;

$R^8$ is independently hydrogen, $C_{1-6}$alkyl, or $C_{1-6}$haloalkyl; wherein said $C_{1-6}$alkyl or $C_{1-6}$haloalkyl is optionally substituted with a group selected from halogen, cyano, $C_{3-6}$cycloalkyl, $C_{3-6}$halo cycloalkyl, $OC_{1-6}$alkyl or $C_{1-6}$alkyl;

$R^9$ is heteroaryl, wherein said heteroaryl is optionally substituted with halogen, cyano, $OR^8$, $C_{1-6}$haloalkyl or $C_{1-6}$alkyl; and $R^{10}$ is hydrogen.

In one embodiment of the present invention,

A is —CH—;

$R^1$ is methyl or ethyl;

$R^2$ is halogen, aryl, heteroaryl or $C_{2-6}$alkynyl, wherein said aryl, heteroaryl or $C_{2-6}$alkynyl is optionally substituted with one to three $R^7$;

$R^5$ and $R^6$ together with the carbon to which they are attached form a cyclohexyl ring, which is substituted with $OR^8$;

$R^7$ is independently halogen, cyano, $OC_{1-6}$alkyl or $C_{2-6}$alkynyl;

$R^8$ is $C_{1-3}$alkyl.

In one embodiment of the present invention,

A is —CH—;

$R^1$ is methyl or ethyl;

$R^2$ is phenyl or pyridinyl, wherein said phenyl or pyridinyl is optionally substituted with one or two $R^7$;

$R^5$ and $R^6$ together with the carbon to which they are attached form a cyclohexyl ring, which is substituted with methoxy;

$R^7$ is independently chloro, fluoro, methoxy, cyano or prop-1-yn-1-yl.

In one embodiment, the compound of formula (I) has the following configuration:

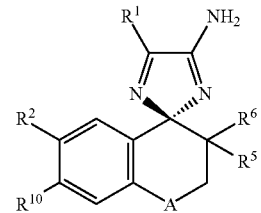

In another embodiment, the invention relates to a compound of formula (I) selected from the group consisting of:

7'-Bromo-5"-methyl-3',4'-dihydrodispiro[cyclopropane-1, 2'-naphthalene-1',2"-imidazol]-4"-amine;

3-(4"-Amino-5"-methyl-3',4'-dihydrodispiro[cyclopropane-1,2'-naphthalene-1',2"-imidazol]-7'-yl)-5-fluorobenzonitrile;

7'-(3,5-Difluorophenyl)-5"-methyl-3',4'-dihydrodispiro[cyclopropane-1,2'-naphthalene-1',2"-imidazol]-4"-amine;

7'-(5-Chloropyridin-3-yl)-5"-methyl-3',4'-dihydrodispiro [cyclopropane-1,2'-naphthalene-1',2"-imidazol]-4"-amine;

(1r,4s)-7'-Bromo-4-methoxy-5"-methyl-3',4'-dihydrodispiro [cyclohexane-1,2'-naphthalene-1',2"-imidazol]-4"-amine;

(1s,4r)-7'-Bromo-4-methoxy-5"-methyl-3',4'-dihydrodispiro [cyclohexane-1,2'-naphthalene-1',2"-imidazol]-4"-amine;

3-[(1r,4s)-4"-Amino-4-methoxy-5"-methyl-3',4'-dihydrodispiro[cyclohexane-1,2'-naphthalene-1',2"-imidazol]-7'-yl]-5-methoxybenzonitrile;

3-[(1s,4r)-4"-Amino-4-methoxy-5"-methyl-3',4'-dihydrodispiro[cyclohexane-1,2'-naphthalene-1',2"-imidazol]-7'-yl]-5-methoxybenzonitrile;

(1r,4s)-7'-(5-Chloropyridin-3-yl)-4-methoxy-5"-methyl-3', 4'-dihydrodispiro[cyclohexane-1,2'-naphthalene-1',2"-imidazol]-4"-amine;

(1s,4r)-7'-(5-Chloropyridin-3-yl)-4-methoxy-5"-methyl-3', 4'-dihydrodispiro[cyclohexane-1,2'-naphthalene-1',2"-imidazol]-4"-amine;

(1s,4r)-4-Methoxy-5"-methyl-7'-[5-(prop-1-yn-1-yl)pyridin-3-yl]-3',4'-dihydrodispiro[cyclohexane-1,2'-naphthalene-1',2"-imidazol]-4"-amine;

(1r,4s)-4-Methoxy-5"-methyl-7'-[5-(prop-1-yn-1-yl)pyridin-3-yl]-3',4'-dihydrodispiro[cyclohexane-1,2'-naphthalene-1',2"-imidazol]-4"-amine;

3-(4"-Amino-5"-methyl-3',4'-dihydrodispiro[cyclopropane-1,2'-naphthalene-1',2"-imidazol]-7'-yl)-5-chlorobenzonitrile;

3-[(1r,4s)-4"-Amino-4-methoxy-5"-methyl-3',4'-dihydrodispiro[cyclohexane-1,2'-naphthalene-1',2"-imidazol]-7'-yl]-5-chlorobenzonitrile;

3-[(1s,4r)-4"-Amino-4-methoxy-5"-methyl-3',4'-dihydrodispiro[cyclohexane-1,2'-naphthalene-1',2"-imidazol]-7'-yl]-5-chlorobenzonitrile;

3-[(1r,4s)-4"-Amino-4-methoxy-5"-methyl-3',4'-dihydrodispiro[cyclohexane-1,2'-naphthalene-1',2"-imidazol]-7'-yl]-5-chlorobenzonitrile; and 3-[(1r,4s)-4"-Amino-4-methoxy-5"-methyl-3',4'-dihydrodispiro[cyclohexane-1,2'-naphthalene-1',2"-imidazol]-7'-yl]-5-chlorobenzonitrile;

or a pharmaceutically acceptable salt of any foregoing compound.

The present invention relates to the use of compounds of formula (I) as hereinbefore defined as well as to the salts thereof. Salts for use in pharmaceutical compositions will be pharmaceutically acceptable salts, but other salts may be useful in the production of the compounds of formula (I).

The compounds of the formula (I) may be administered in the form of a prodrug which is broken down in the human or animal body to give a compound of the formula (I). Examples of prodrugs include in vivo hydrolysable esters of a compound of the formula (I). An in vivo hydrolysable (or cleavable) ester of a compound of the formula (I) that contains a carboxy or a hydroxy group is, for example, a pharmaceutically acceptable ester which is hydrolysed in the human or animal body to produce the parent acid or alcohol. Various forms of prodrugs are known in the art.

The definitions set forth in this application are intended to clarify terms used throughout this application. The term "herein" means the entire application.

A variety of compounds in the present invention may exist in particular geometric or stereoisomeric forms. The present invention takes into account all such compounds, including tautomers, cis- and trans isomers, R- and S-enantiomers, diastereomers, (D)-isomers, (L)-isomers, the racemic mixtures thereof, and other mixtures thereof, as being covered within the scope of this invention. Additional asymmetric carbon atoms may be present in a substituent such as an alkyl group. All such isomers, as well as mixtures thereof, are intended to be included in this invention. The compounds herein described may have asymmetric centers. Compounds of the present invention containing an asymmetrically substituted atom may be isolated in optically active or racemic forms. It is well known in the art how to prepare optically active forms, such as by resolution of racemic forms, by synthesis from optically active starting materials, or synthesis using optically active reagents. When required, separation of the racemic material can be achieved by methods known in the art. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

As used herein, "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the non-toxic salts or the quaternary ammonium salts of the parent compound formed, for example, from non-toxic inorganic or organic acids. For example, such non-toxic salts include those derived from inorganic acids such as hydrochloric acid.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like diethyl ether, ethyl acetate, ethanol, isopropanol, or acetonitrile are used.

The present invention further includes all tautomeric forms of compounds of the invention. As used herein, "tautomer" means other structural isomers that exist in equilibrium resulting from the migration of a hydrogen atom. For example, keto-enol tautomerism where the resulting compound has the properties of both a ketone and an unsaturated alcohol. Other examples of tautomerism include 2H-imidazole-4-amine and its tautomer 1,2-dihydroimidazol-5-imine, and 2H-imidazol-4-thiol and its tautomer 1,2-dihydroimidazol-5-thione. It is understood that in compound representations throughout this description, only one of the possible tautomers of the compound is drawn or named.

As used herein "stable compound" and "stable structure" are meant to indicate a compound that is sufficiently robust to survive isolation to a useful degree of purity from a reaction mixture, and formulation into an efficacious therapeutic agent.

Compounds of the invention further include hydrates and solvates.

The present invention further includes isotopically-labeled compounds of the invention. An "isotopically" or "radiolabeled" compound is a compound of the invention where one or more atoms are replaced or substituted by an atom having an atomic mass or mass number different from the atomic mass or mass number typically found in nature (i.e., naturally occurring). Suitable isotopes that may be incorporated in compounds of the present invention include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labelled compounds will depend on the specific application of that radio-labelled compound. For example, for in vitro receptor labelling and competition assays, compounds that incorporate $^3$H, $^{14}$C, $^{82}$Br, $^{125}$I, $^{131}$I or $^{35}$S will generally be most useful. For radio-imaging applications $^{11}$C, $^{18}$F, $^{125}$I, $^{123}$I, $^{124}$I, $^{131}$I $^{75}$Br, $^{76}$Br or $^{77}$Br will generally be most useful.

It is understood that a "radio-labeled compound" is a compound that has incorporated at least one radionuclide. In some embodiments the radionuclide is selected from the group consisting of $^3$H, $^{14}$C, $^{125}$I, $^{35}$S and $^{82}$Br.

Compounds of the present invention may be administered orally, by parenteral, buccal, vaginal, rectal, inhalation, or insufflation administration, sublingually, intramuscularly, subcutaneously, topically, intranasally, intraperitoneally, intrathoracically, intravenously, epidurally, intrathecally, intracerebroventricularly and by injection into the joints.

The dosage will depend on the route of administration, the severity of the disease, age and weight of the patient and other factors normally considered by the attending physician, when determining the individual regimen and dosage level as the most appropriate for a particular patient.

The quantity of the compound to be administered will vary for the patient being treated and will vary from about 100 ng/kg of body weight to 100 mg/kg of body weight per day. For instance, dosages can be readily ascertained by those skilled in the art from this disclosure and the knowledge in the art. Thus, the skilled artisan can readily determine the amount of compound and optional additives, vehicles, and/or carrier in compositions and to be administered in methods of the invention.

In another aspect, the invention relates to a compound of formula (I), or a pharmaceutically acceptable salt thereof, for use as a medicament, e.g. for treatment or prevention of Aβ-related pathologies.

In another aspect, the invention relates to the use of a compound of formula (I), or a pharmaceutically acceptable salt thereof, in the manufacture of a medicament for treatment or prevention of Aβ-related pathologies.

In another aspect, the invention relates to a method of treating or preventing Aβ-related pathologies in a mammal, such as a human being, comprising administering to a mammal in need thereof a therapeutically effective amount of a compound of Formula (I), or a pharmaceutically acceptable salt thereof.

The compounds of the invention, and their pharmaceutically acceptable salts, thereby provide methods of treatment of Aβ-related pathologies, such as, but not limited to, Alzheimer's disease, Down's syndrome, β-amyloid angiopathy, cerebral amyloid angiopathy, hereditary cerebral hemorrhage, a disorder associated with cognitive impairment, MCI ("mild cognitive impairment"), memory loss, attention deficit symptoms associated with Alzheimer's disease, neurodegeneration associated with Alzheimer's disease, dementia of mixed vascular origin, dementia of degenerative origin, presenile dementia, senile dementia, dementia associated with Parkinson's disease, progressive supranuclear palsy traumatic brain injury and cortical basal degeneration.

In another aspect, the invention relates to a pharmaceutical composition comprising as active ingredient a therapeutically effective amount of a compound of formula (I), or a pharmaceutically acceptable salt thereof, in association with at least one pharmaceutically acceptable excipient, carrier or diluent.

In another aspect, the invention relates to a method of inhibiting activity of BACE with a compound according to formula (I).

In another aspect, the invention relates to a method of treating or preventing an Aβ-related pathology in a mammal, such as a human being, comprising administering to said patient a therapeutically effective amount of a compound according to formula (I), or a pharmaceutically acceptable salt thereof, and at least one cognitive enhancing agent, memory enhancing agent, or cholinesterase inhibitor, wherein said Aβ-related pathology is Alzheimer's disease.

In another aspect, the invention relates to a pharmaceutical composition comprising (i) a compound of formula (I), or a pharmaceutically acceptable salt thereof, (ii) an additional therapeutic agent, or a pharmaceutically acceptable salt thereof, and (iii) pharmaceutically acceptable excipients, carriers or diluents.

In another aspect, the invention relates to a pharmaceutical composition comprising (i) a compound of formula (I), or a pharmaceutically acceptable salt thereof, (ii) at least one agent selected from the group consisting of cognitive enhancing agents, memory enhancing agents and cholinesterase inhibitors, and (iii) pharmaceutically acceptable excipients, carriers or diluents.

The treatment of Aβ-related pathology defined herein may be applied as a mono therapy or may involve, in addition to the compound of the invention, conjoint treatment with conventional therapy of value in treating one or more disease conditions referred to herein. Such conventional therapy may include one or more of the following categories of agents: acetyl cholinesterase inhibitors, anti-inflammatory agents, cognitive and/or memory enhancing agents or atypical antipsychotic agents. Cognitive enhancing agents, memory enhancing agents and acetyl choline esterase inhibitors includes, but not limited to, donepezil (ARICEPT), galantamine (REMINYL or RAZADYNE), rivastigmine (EXELON), tacrine (COGNEX) and memantine (NAMENDA, AXURA or EBIXA). Atypical antipsychotic agents includes, but not limited to, olanzapine (marketed as ZYPREXA), aripiprazole (marketed as ABILIFY), risperidone (marketed as RISPERDAL), quetiapine (marketed as SEROQUEL), clozapine (marketed as CLOZARIL), ziprasidone (marketed as GEODON) and olanzapine/fluoxetine (marketed as SYMBYAX).

Such conjoint treatment may be achieved by way of the simultaneous, sequential or separate dosing of the individual components of the treatment. Such combination products employ the compounds of the invention.

Additional conventional chemotherapy may include one or more of the following categories of agents: (i) antidepressants, (ii) atypical antipsychotics, (iii) antipsychotics, (iv) anxiolytics, (v) anticonvulsants, (vi) currently used Alzheimer's therapies, (vii) Parkinson's therapies, (viii) migraine therapies, (ix) stroke therapies, (x) urinary incontinence therapies, (xi) neuropathic pain therapies, (xii) nociceptive pain therapies, (xiii) insomnia therapies and (xiv) mood stabilizers. Known treatments for the foregoing therapies may be employed in combination with the invention described herein.

Such combination products employ the compounds of this invention within the dosage range described herein and the other pharmaceutically active compound or compounds within approved dosage ranges and/or the dosage described in the publication reference.

Preparation of Compounds

The compounds of the present invention can be prepared as a free base or a pharmaceutically acceptable salt thereof by the processes described below. Throughout the following description of such processes it is understood that, where appropriate, suitable protecting groups will be added to, and subsequently removed from the various reactants and intermediates in a manner that will be readily understood by one skilled in the art of organic synthesis. Conventional procedures for using such protecting groups as well as examples of suitable protecting groups are for example described in *Protective Groups in Organic Synthesis* by T. W. Greene, P. G. M Wutz, $3^{rd}$ Edition, Wiley-Interscience, New York, 1999. It is understood that microwaves (MW) can alternatively be used for the heating of reaction mixtures.

Another aspect of the present invention provides a process for preparing a compound of formula (I), or a pharmaceutically acceptable salt thereof, wherein, unless specified otherwise, $R^1$-$R^{10}$, and A are defined as for formula (I) above, or are groups that can be converted into $R^1$-$R^{10}$, or A in subsequent transformations. A compound of formula (XI) may be equivalent to a compound of formula (I). LG represents a leaving group such as halogen (such as chlorine, bromine or iodine) or an alkyl-, aryl- or haloalkyl-sulfonate (such as triflate) and PG represents a protecting group. Said process comprises of:

Method (i): Formation of a Corresponding Compound of Formula (IIIa):

Scheme 1

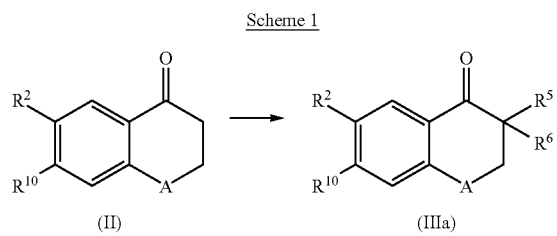

(II)          (IIIa)

A ketone of formula (II), is treated with a suitable base such as sodium hydride, KOtBu, or LDA in presence of a suitable electrophile such as methyl acrylate, (2-chloroethyl)dimethylsulfonium iodide, a (bis-substituted) alkyl halide, triflate or mesylate to give a compound of formula (IIIa) (Scheme 1). Said reaction may be performed at a temperature range between 0° C. and +90° C., in a suitable solvent, such as tetrahydrofuran, 2-Me THF or dimethylformamide. Alkyations could be carried out in a sequential way with intermediates isolated and purified or in a one-pot stepwise fashion. If the reactions yield a product substituted with an ester, olefin, cyano, sulfone, sulfonium ion or the like it could optionally be reacted further by Dieckman cyclization, RCM, nucleophilic substitution or cycloaddition to give highly substituted spirocyclic intermediates. The resulting spirocyclic ring may optionally contain one or more substituent which may be further converted by known functional group transformations, such as for example decarboxylation, reduction of a ketone to an alcohol and conversion of an alcohol to an alkylether.

Method (ii): Formation of a Corresponding Compound of Formula (IIIa):

Scheme 2

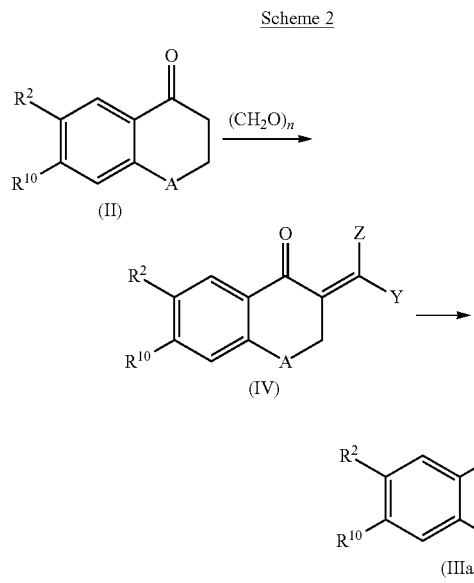

A ketone of formula (II), is reacted with an aldehyde or ketone such as formaldehyde in a temperature range between room temperature and +100° C. in presence of any protic acid such as a boronic acid (such as PhB(OH)$_2$), or in the presence of N-Methylanilinium trifluoroacetate, in a suitable solvent such as benzene or toluene (Scheme 2). The intermediate (IV), wherein Z and Y are defined as for example hydrogen or alkyl, can be reacted with various dienes utilizing the Diels-Alder reaction in a temperature range between room temperature and +220° C. optionally in a sealed tube. The reaction can be carried out neat or in a suitable solvent such as benzene, toluene or THF. A Lewis acid or any other agents that may assist the reaction can be added to yield enriched enantiomers or diastereomers. The resulting spirocyclic ring may optionally contain one or more substituent which may be further converted by known functional group transformations, such as for example decarboxylation, reduction of a ketone to an alcohol and conversion of an alcohol to an alkylether.

Method (iii) Formation of a Corresponding Compound of Formula (XV):

Scheme 3

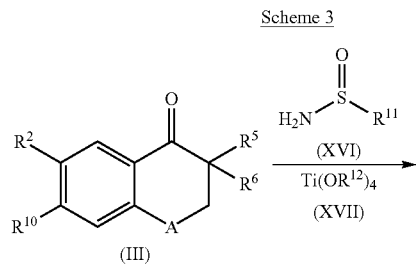

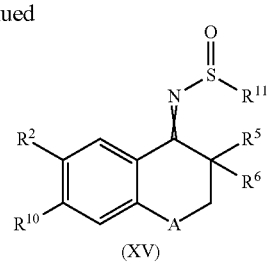

A compound of formula (XV) may be obtained by reacting a compound of formula (III) with a compound of formula (XVI) (Scheme 3), wherein R$^{11}$ is alkyl (such as for example tert-butyl). The reaction is performed in the presence of a suitable Lewis acid, such as a compound of formula (XVII), wherein R$^{12}$ is alkyl (such as ethyl or isopropyl). The reaction is performed in a suitable solvent (such as dichloromethane, 2-methyl-tetrahydrofuran or tetrahydrofuran) at a temperature between room temperature and reflux temperature, optionally with azeotropic distillation to remove an alcohol formed in the reaction.

Method (iv) Formation of a Corresponding Compound of Formula (XIa):

Scheme 4

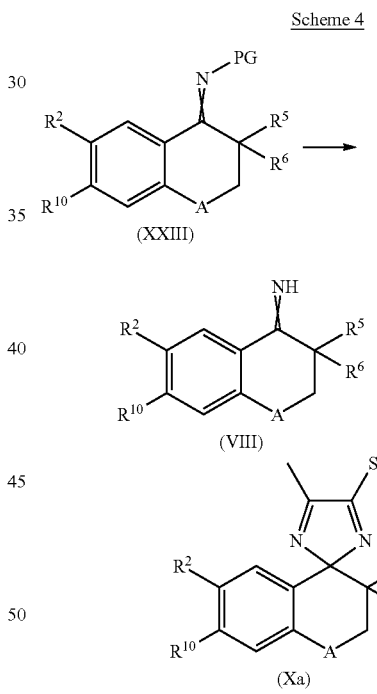

A compound of formula (VIII) may be obtained by reacting a compound (XXIII) (wherein PG is a protecting group such as for example S(O)R$^{11}$ (Method (iii), formula XV), using a suitable method of removing the protecting group PG to form imine (VIII) (Scheme 4). A suitable method may be, but is not limited to, treating said compound (XXIII) with an acid such as hydrochloric acid under dry conditions in a suitable solvent (such as dioxane or tetrahydrofuran). Compound (VIII) may be isolated or reacted further without isolation. A compound of formula (VIII) is further reacted with 2-oxopropane thioamide (described in Asinger et al. *Justus Liebigs Annalen der Chemie* 1971, vol 744, p. 51-64) optionally in the presence of triethyl orthoformate, in a solvent such as methanol at a temperature between room temperature and reflux temperature, optionally under Dean-Stark conditions, to yield a compound of formula (Xa). The transformation to a compound of formula (XIa) may be performed by reacting the intermediate of formula (Xa) with ammonia, optionally in the presence of an oxidation agent, such as tert-butyl hydroperoxide. If 2-oxopropane thioamide is exchanged for 2-oxobutanethioamide in the process described by Scheme 4, the compounds of formula (Xb) and (XIb) will be obtained instead of (Xa) and (XIa).

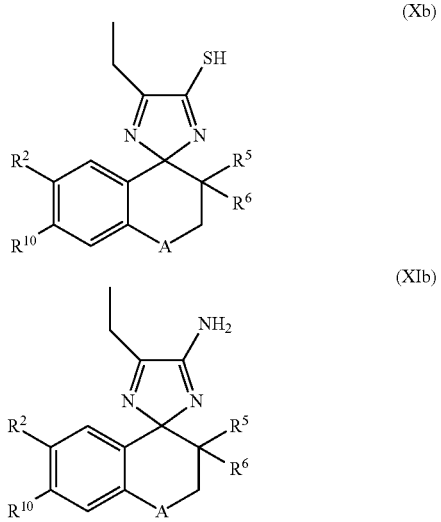

(Xb)

(XIb)

Method (v) Formation of a Corresponding Compound of Formula (XIa):

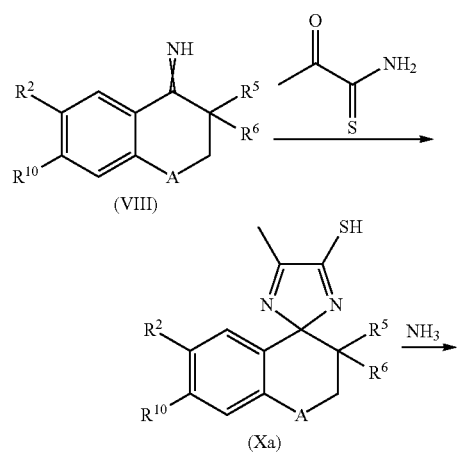

Scheme 5

(VIII)

(Xa)

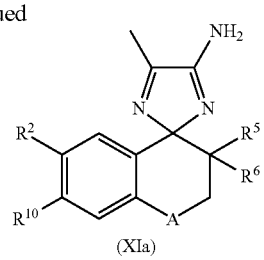

(XIa)

A compound of formula (Xa) may be obtained from a compound of formula (VIII) (Scheme 5). An imine of formula (VIII) is reacted with 2-oxopropane thioamide (described in Asinger et al. *Justus Liebigs Annalen der Chemie* 1971, vol 744, p. 51-64) in a solvent such as methanol at a temperature between room temperature and reflux temperature to yield a compound of formula (Xa). Compound (VIII) may be obtained from a ketone of formula (III) (Scheme 4) or prepared by methods known to the person skilled in the art. The compound of formula (Xa) is subsequently treated with ammonia, to yield the compound of formula (XIa). If 2-oxopropane thioamide is exchanged for 2-oxobutanethioamide in the process described by Scheme 5, the compounds of formula (Xb) and (XIb) will be obtained instead of (Xa) and (XIa) (see above).

Method (vi) Formation of a Corresponding Compound of Formula (XIa):

Scheme 6

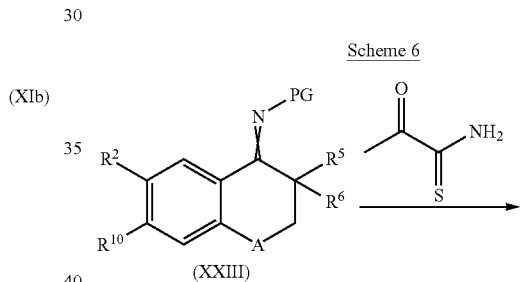

(XXIII)

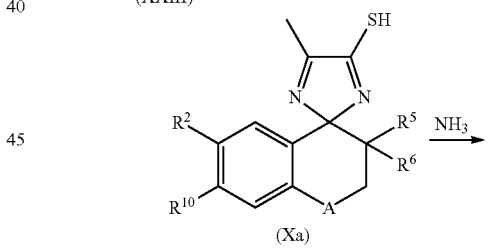

(Xa)

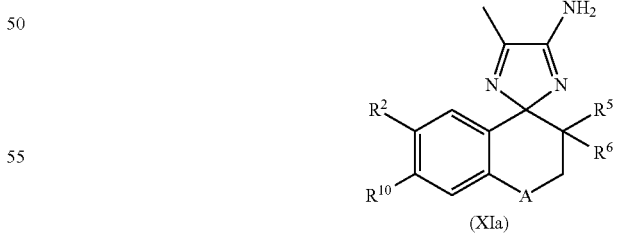

(XIa)

A compound of formula (XXIII) (wherein PG is a protecting group such as for example S(O)R[11] (Method (vii), formula XV), is reacted with 2-oxopropane thioamide (described in Asinger et al. *Justus Liebigs Annalen der Chemie* 1971, vol 744, p. 51-64) in a solvent such as acetonitrile at a temperature range between +100° C. and +160° C. to yield a compound of formula (Xa) (Scheme 6). The compound of formula (Xa) is subsequently treated with ammonia, in a suitable solvent such as methanol, THF, or 2-methyl-tetrahydrofuran optionally in the presence of an oxidation agent, such as tert-butyl hydroperoxide, at a temperature between room temperature and 150° C., optionally in a closed system, to yield the compound of formula (XIa). If 2-oxopropane thioamide is exchanged for 2-oxobutanethioamide in the process described by Scheme 6, the compounds of formula (Xb) and (XIb) (see above) will be obtained instead of (Xa) and (XIa).

Method (vii) Formation of a Corresponding Compound of Formula (I):

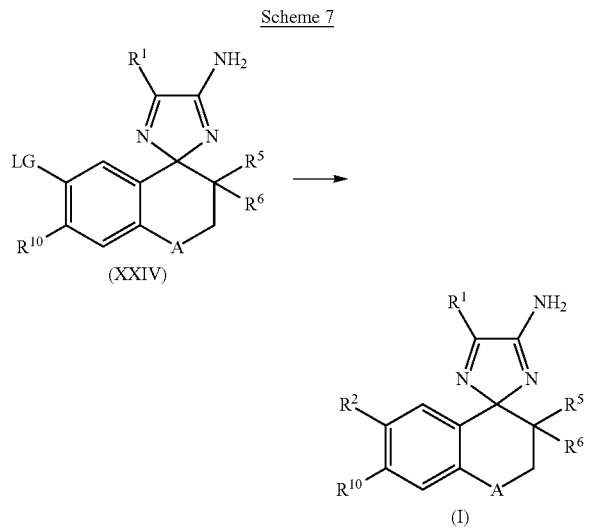

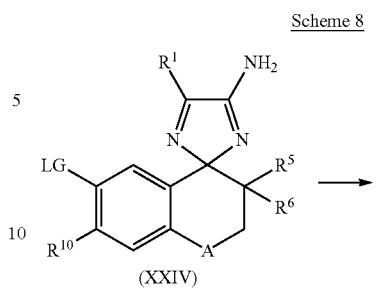

A compound of formula (I) wherein $R^2$ is an optionally substituted aryl or heteroaryl, may be obtained (Scheme 7) by starting from, for example, a compound of formula (XXIV), and reacting said compound of formula (XXIV) with a boronic acid or a boronic ester or a stannane of formula T-$R^2$, wherein T is for example $B(OH)_2$, $B(Oalkyl)_2$, or $SnR_3$, and $R^2$ is an optionally substituted aryl or a heteroaryl, in the presence of a transition metal catalyst such as a palladium catalyst, such as [1,1'-bis(diphenylphosphino)ferrocene]palladium(II) chloride, tetrakis(triphenylphosphine)-palladium(0), palladium diphenylphosphineferrocene dichloride, palladium(II) acetate or bis(dibenzylideneacetone) palladium (0), or sodium tetrachloropalladate (II). Optionally, a suitable ligand such as triphenylphosphine, tri-tert-butylphosphine or 2-(dicyclohexylphosphino)biphenyl, 3-(di-tert-butylphosphonium)propane sulfonate, or zinc and sodium triphenylphosphinetrimetasulfonate, is used. A suitable base, such as cesium fluoride, an alkyl amine, such as triethyl amine, or an alkali metal or alkaline earth metal carbonate or hydroxide such as potassium carbonate, sodium carbonate, cesium carbonate, or sodium hydroxide, may be used in the reaction. Said reaction may be performed in a suitable solvent, such as toluene, tetrahydrofuran, 2-methyl-tetrahydrofuran, dioxane, dimethoxyethane, water, ethanol, N,N-dimethylacetamide, acetonitrile or N,N-dimethylformamide, or mixtures thereof.

Alternatively a compound of formula (I) wherein $R^2$ is an optionally substituted aryl or heteroaryl can be prepared from compound (XXIV) by transformation into a compound (Ia) wherein T is as described above ($B(OH)_2$ or $B(Oalkyl)_2$) (Scheme 8). Compound (Ia) is then reacted with a compound $R^2$-LG wherein $R^2$ is an optionally substituted aryl or heteroaryl and LG is a leaving group such as a halogen to yield compound (I).

Method (viii) Formation of a Corresponding Compound of Formula (I):

A compound of formula (I), wherein $R^2$ is cyano, may be obtained (Scheme 7) by starting from, for example, a compound of formula (XXIV), wherein LG is a leaving group such as a halogen, (such as iodide, bromide or chlorine), and reacting said compound of formula (XXIV) with a metal cyano reagent such as copper(I) cyanide.

Method (ix) Formation of a Corresponding Compound of Formula (I):

A compound of formula (I), wherein $R^2$ is an alkyl group such as methyl may be generated from a compound of formula (XXIV) (Scheme 7), wherein LG represents a leaving group, such as a halogen, (such as iodide, bromide or chlorine), by reaction with an organometallic reagent generated from zinc iodide and methylmagnesium bromide under the influence of a transition metal catalyst such as for example bis(triphenylphosphine)palladium(II) chloride.

Method (x) Formation of a Corresponding Compound of Formula (I):

A compound of formula (I), wherein $R^2$ is an alkyne may be generated from a compound of formula (XXIV) (Scheme 7), wherein LG represents a leaving group, such as a halogen, (such as iodide or bromide), by reaction with an alkyne such as an alkylethyne or a cycloalkylethyne under the influence of a transition metal catalyst such as for example tetrakis(triphenylphosphine)palladium(0) in presence of a base such as triethylamine and copper(I)iodide. The alkyne is optionally silylated. Said reaction may be performed at a temperature range between room temperature and reflux temperature, in a suitable solvent, such as THF or toluene.

Method (xi) Formation of a Corresponding Compound of Formula (I):

A compound of formula (I) wherein $R^2$ is $NHC(O)R^9$ may be prepared according to Scheme 7 by reacting a compound of formula (XXIV) with a compound $R^9C(O)NH_2$ in the presence of a suitable palladium catalyst such as palladium (II) acetate, optionally in the presence of a suitable ligand such as Xantphos. The reaction is performed in the presence of a suitable base such as cesium carbonate in a suitable solvent such as THF or 2-methyl-tetrahydrofuran at a temperature between reflux temperature and 160° C.

Method (xii) Formation of a Corresponding Compound of Formula (I):

A compound of formula (I) wherein $R^2$ is $NHC(O)R^9$ may be obtained from a compound of formula (XXIV) as shown in Scheme 9.

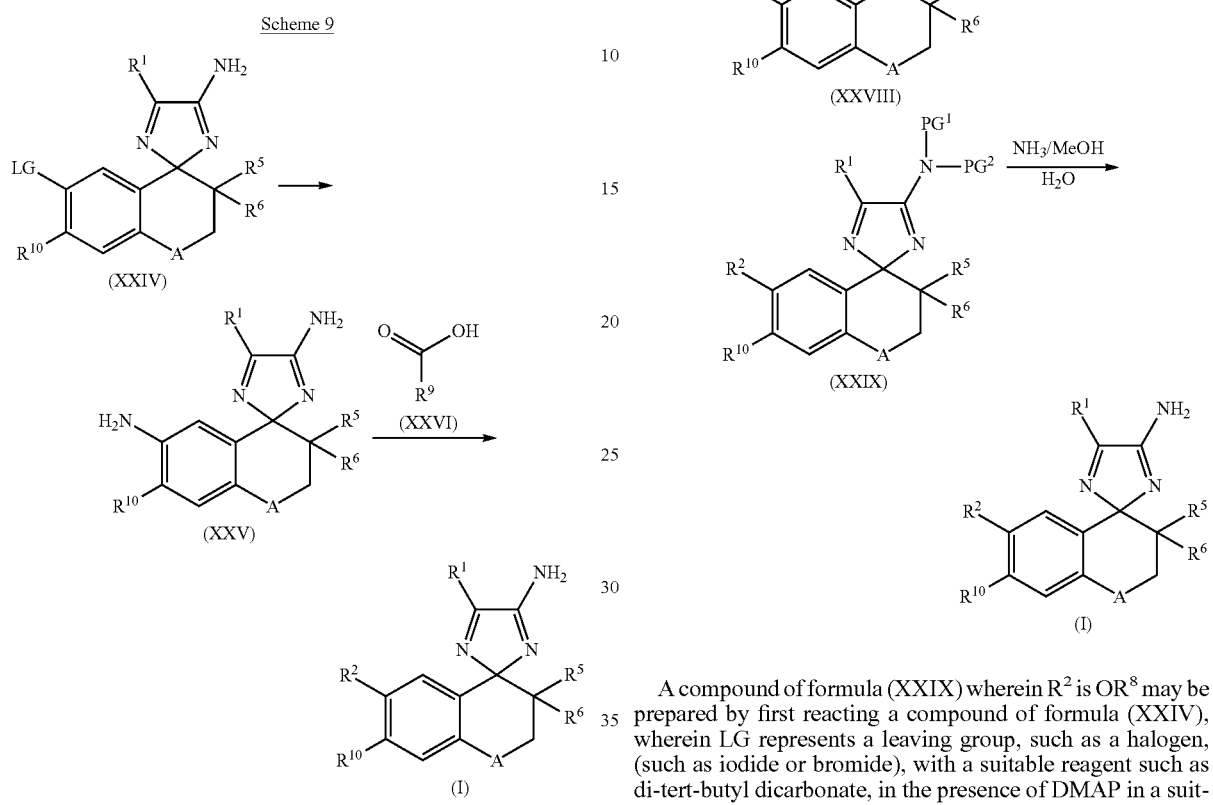

A compound of formula (XXIV) is reacted with ammonia in the presence of trans-4-hydroxy-L-proline, potassium carbonate and copper(I)iodide in a solvent such as DMSO at a temperature between room temperature and 150° C. to give a compound of formula (XXV). Said compound of formula (XXV) is further reacted with a carboxylic acid of formula (XXVI) wherein $R^9$ is as defined above. The reaction is performed in the presence of a suitable amide coupling agent such as 1-(3-dimethylaminopropyl)-3-ethyl-carbodiimide in a solvent such as DMF, optionally in the presence of hydrochloric acid.

Method (xiii) Formation of a Compound of Formula (I)

Scheme 10

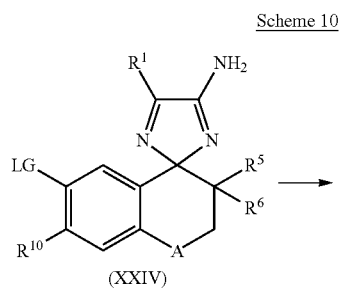

A compound of formula (XXIX) wherein $R^2$ is $OR^8$ may be prepared by first reacting a compound of formula (XXIV), wherein LG represents a leaving group, such as a halogen, (such as iodide or bromide), with a suitable reagent such as di-tert-butyl dicarbonate, in the presence of DMAP in a suitable solvent such as dichloromethane at a temperature between 0° C. and reflux to yield a compound of formula (XXVIII) wherein $PG^1$ and/or $PG^2$ represents hydrogen and/or a suitable protecting group such as tert-butoxycarbonyl (Scheme 10). Subsequently compound (XXVIII) is reacted with an alcohol of formula (XXVII) in the presence of a suitable palladium catalyst such as palladium(II) acetate, optionally in the presence of a suitable ligand such as di-tert-butyl(2',4',6'-triisopropyl-3-methoxy-6-methylbiphenyl-2-yl)phosphine or 2-(di-t-butylphosphino)-1,1'-binaphthyl (Scheme 10). The reaction is performed in the presence of a suitable base such as cesium carbonate in a suitable solvent such as THF, 2-methyl-tetrahydrofuran or toluene at a temperature between 20° C. and 160° C. The compound of formula (I) may be obtained from a compound of formula (XXVIII) by reacting it with a solution of $NH_3$, such as in methanol, in the presence of water, at a temperature between 60° C. and 100° C.

Compounds of formula (II), (III), (XVI), (XVII), (XXVI), and (XXVII) are commercially available compounds, or are known in the literature, or they are prepared by standard processes known in the art.

General Methods

All solvents used were of analytical grade and commercially available anhydrous solvents were routinely used for reactions. Starting materials used were available from commercial sources, or prepared according to literature procedures. Room temperature refers to 20-25° C. Solvent mixture compositions are given as volume percentages or volume ratios.

Microwave heating was performed in a Biotage Creator, Initiator or Smith Synthesizer Single-mode microwave cavity producing continuous irradiation at 2450 MHz. It is understood that microwaves can be used for the heating of reaction mixtures.

Thin layer chromatography (TLC) was performed on Merck TLC-plates (Silica gel 60 $F_{254}$) and spots were UV visualized. Straight phase flash column chromatography ("flash chromatography") was manually performed on Merck Silica gel 60 (0.040-0.063 mm), or automatically using an ISCO Combiflash® Companion™ system using RediSep™ normal-phase flash columns using the solvent system indicated. Phase separation was optionally performed on an Isolute® phase separator.

NMR

NMR spectra were recorded on a 400-600 MHz NMR spectrometer fitted with a probe of suitable configuration. Spectra were recorded at ambient temperature unless otherwise stated. Chemical shifts are given in ppm down- and upfield from TMS (0.00 ppm). The following reference signals were used in $^1$H-NMR: TMS δ 0.00, or the residual solvent signal of DMSO-$d_6$ δ 2.49, $CD_3OD$ δ 3.30, acetone-$d_6$ 2.04 or $CDCl_3$ δ 7.25 (unless otherwise indicated). Resonance multiplicities are denoted s, d, t, q, m, br and app for singlet, doublet, triplet, quartet, multiplet, broad and apparent, respectively. In some cases only diagnostic signals are reported.

HPLC, HPLCMS, and LCMS Analyses:

High pressure liquid chromatography (HPLC) was performed on a reversed phase (RP) column. A linear gradient was applied using for example mobile phase A (10 mM $NH_4OAc$ in 5% $CH_3OH$ or 5% $CH_3CN$ (aq.), or 0.1% $NH_3$ (aq.) or 0.1% formic acid (aq.)) and B ($CH_3OH$ or $CH_3CN$). Mass spectrometry (MS) analyses were performed in positive and/or negative ion mode using electrospray ionization (ESI+/−) and/or atmospheric pressure chemical ionization (APCI+/−).

GCFID and GCMS Analyses:

Gas chromatography (GC) was performed on a GC equipped with a mass spectrometer (MS) or a flame ionization detector (FID). The MS ion source was either an electron impact (EI) or a chemical ionization (CI, reactant gas methane). For separation a capillary column was used for example DB-5MS, (J&W Scientific). A linear temperature gradient was applied.

Preparative Chromatography:

Preparative chromatography was run on a Waters Fraction-Lynx system with a Autosampler combined Automated Fraction Collector (Waters 2767), Gradient Pump (Waters 2525), Column Switch (Waters CFO) and PDA (Waters 2996). Column; XBridge® Prep C8 10 μm OBD™ 19×300 mm, with guard column; XTerra® Prep MS C8 10 μm 19×10 mm Cartridge. A gradient of A (95% 0.1 M $NH_4OAc$ in MilliQ water and 5% MeCN) in B (100% MeCN) or a gradient of A (95% 0.1 M $NH_4OAc$ in MilliQ water and 5% MeOH), A (0.2% $NH_3$ in MilliQ water) or A (0.2% formic acid in MilliQ water) in B (100% MeOH) was applied for LC-separation at flow rate 20 ml/min. Preparative chiral chromatography for separation of isomers was run on for example an LaPrep® system using the specified column and mobile phase system.

SFC Analyses:

Supercritical Fluid Chromatography (SFC) was performed on a straight phase column. A isocratic flow was applied using mobile phase A ($CO_2$) and for example mobile phase B (MeOH, EtOH or IPA).

Straight Phase HPLC Analyses:

High pressure liquid chromatography (HPLC) was performed on a straight phase column. A linear gradient or isocratic flow was applied using for example mobile phase A (Heptane) and B (EtOH or IPA).

High-Resolution Mass Spectrometry (HRMS) for accurate mass measurements was performed on a Waters Synapt-G2 mass spectrometer equipped with a LockSpray source and connected to an Acquity UPLC system with a PDA detector and an Acquity UPLC BEH C18 column. The measured mass confirmed the elemental composition within 3 ppm.

ABBREVIATIONS

ACN acetonitrile
aq aqueous
Atm atmospheric pressure
Boc t-butoxycarbonyl
Borax di-sodium tetraborate or sodium borate or sodium tetraborate
Cbz benzyloxycarbonyl
CDI 1,1'-carbonyldiimidazole
dba dibenzylideneacetone
DCM dichloromethane
DEA diethylamine
DIBAL-H diisobutylaluminium hydride
DIPEA diisopropylethylamine
DMAP 4-Dimethylaminopyridine
DME 1,2-dimethoxyethane
DMF N,N-dimethyl formamide
DMSO dimethyl sulfoxide
dppf 1,1'-bis(diphenylphosphino)ferrocene
$Et_2O$ diethyl ether
EtOAc ethyl acetate
EtOH ethanol
eq. or equiv. equivalent
h hour(s)
HPLC high performance liquid chromatography
IPA isopropanol
LCMS liquid chromatography mass spectrometry
LiHMDS lithium bis(trimethylsilyl)amide
MeOH methanol
min minute(s)
MS mass spectrometry
MW microwave(s)
$NH_4OAc$ ammonium acetate
NMR nuclear magnetic resonance
ox oxidation
Psi pounds per square inch
quant. quantitative
RCM ring closing metathesis
r.t. room temperature
sat. saturated
SFC supercritical fluid chromatography
TFA trifluoroacetic acid
THF tetrahydrofuran
TLC thin layer chromatography
TMEDA tetramethylethylenediamine
UPLC ultra performance liquid chromatography
2-Me THF 2-methyl tetrahydrofuran Compounds have been named using CambridgeSoft MedChem ELN v2.2 or ACD/Name, version 10.0, or 10.06, or version 12.01, software from Advanced Chemistry Develop-

INTERMEDIATES

Intermediate 1

2-Oxopropanethioamide

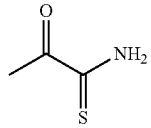

To a −10° C. solution of THF (1700 mL) and acetyl cyanide (250 mL, 3.15 mol) was H$_2$S bubbled for approx 45 min. The bubbling was stopped, and the solution was stirred until the temp. was −10° C. More H$_2$S was bubbled until the temperature was stable at −10° C. Triethylamine (2.2 mL, 15.8 mmol) in THF (20 mL) was added dropwise (very exothermic reaction) at such rate that temp. was kept between 0° C. and −3° C. After addition was completed, the temp. was set to +4° C. and the mixture was stirred overnight. Nitrogen was flushed through the reaction for 30 min and the mixture was concentrated to give the title product (319 g, 98% yield). $^1$H NMR (500 MHz, CDCl$_3$) δ ppm 2.67 (s, 3 H), 7.30-7.81 (m, 1 H), 7.97-8.52 (m, 1 H); $^{13}$C NMR (126 MHz, CDCl$_3$) δ ppm 25.1, 190.8, 192.5; MS (ES+) m/z 104 [M+H]$^+$.

Intermediate 2

3-Bromo-5-(prop-1-ynyl)pyridine

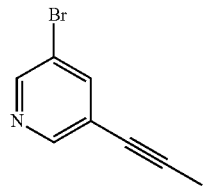

3,5-Dibromopyridine (30 g, 127 mmol), copper(I) iodide (7.24 g, 38.0 mmol) and tetrakis(triphenylphosphine)palladium(0) (4.39 g, 3.80 mmol) were mixed in toluene (120 mL) under nitrogen atmosphere. 1-(Trimethylsilyl)-1-propyne (26.36 mL, 164.5 mmol), triethylamine (53.0 mL, 380 mmol) and tetra-n-butylammonium fluoride (12.66 mL, 12.66 mmol) were added. The mixture was heated to reflux and stirred under nitrogen overnight. Water (100 mL) was added to the reaction mixture was filtered and the phases separated. The organic phase was washed with 1 M HCl aq. (100 mL). The organic phase was concentrated and dissolved in MeOH (200 mL), filtered and concentrated. The mixture was dissolved in DCM and evaporated with silica gel to dryness, and then transferred to a silica gel column (300 g). The product was eluted with a gradient of EtOAc (0-5%) in heptane. The fractions containing the pure product was combined and evaporated to give the title compound (16.39 g, 66% yield): $^1$H NMR (500 MHz, CDCl$_3$) δ ppm 2.08 (s, 3 H), 7.82 (t, 1 H), 8.52 (d, 1 H), 8.55 (d, 1 H); MS (APCI+) m/z 197.0 [M+H]$^+$.

Intermediate 3

5-(Prop-1-ynyl)pyridin-3-ylboronic acid

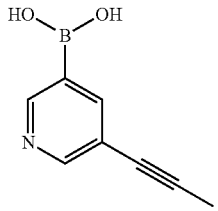

3-Bromo-5-(prop-1-ynyl)pyridine (Intermediate 2, 25 g, 117 mmol), 2-methyl-tetrahydrofuran (60 mL), toluene (200 mL) and triisopropyl borate (33.2 mL, 140.78 mmol) were mixed. The mixture was cooled to −50° C. To the cold mixture was added n-BuLi (59.8 mL, 149.5 mmol) dropwise during 30 min. The mixture was stirred for 60 min. at −50° C. 2M HCl aq. (100 mL) was added. The mixture was then allowed to reach r.t. and stirred for 20 min. The organic and water phase were separated. The organic phase was extracted with NaOH (2M aq.) (2×100 mL). The water phases were combined and the pH was adjusted to pH 5. The product was extracted with 2-methyl-THF (2×100 mL). The organic phase was dried with Na$_2$SO$_4$, filtered and concentrated to give the title compound (16.47 g, 87% yield): $^1$H NMR (500 MHz, CD$_3$OD) δ ppm 2.11 (s, 3 H) 8.21 (br. s., 1 H) 8.53 (m, 2 H); MS (APCI+) m/z 162.2 [M+H]$^+$.

Intermediate 4

3-Chloro-5-(4,4,5,5-tetramethyl-1,3,2-dioxaborolan-2-yl)benzonitrile

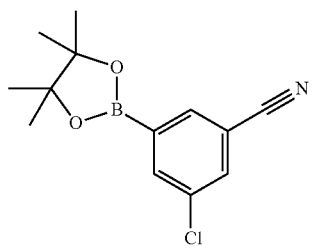 [SMILES: CC1(C)OB(c2cc(Cl)cc(C#N)c2)OC1(C)C]

A suspension of 4,4,4',4',5,5,5',5'-octamethyl-2,2'-bi(1,3,2-dioxaborolane) (665 mg, 2.62 mmol), 3-chloro-5-iodobenzonitrile (345 mg, 1.31 mmol), and potassium acetate (386 mg, 3.93 mmol) in dioxane (5 mL) was degassed with a stream of argon for a couple of min. PdCl$_2$(dppf) CH$_2$Cl$_2$ (53.5 mg, 0.07 mmol) was added and the mixture was heated at reflux under N$_2$ for 4 h. The mixture was allowed to cool and was then filtered. The filter cake was washed with EtOAc. The filtrate was concentrated in vacuo. The residue was purified by flash chromatography (eluent: heptane/EtOAc gradient) affording the title compound (69 mg, 20% yield). $^1$H NMR (400 MHz, DMSO-d$_6$) δ ppm 1.30 (s, 12 H), 7.88 (dd, 1 H), 7.90-7.94 (m, 1 H), 8.19 (dd, 1 H); MS (CI) m/z 264

Intermediate 5

(2-Chloroethyl)dimethylsulfonium iodide

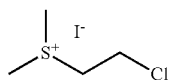

A solution of 2-chloroethyl methyl sulfide (2.00 mL, 22.1 mmol) in iodomethane (8.60 mL, 139 mmol) was stirred at r.t. for 65 h. The resulting solid was filtered, washed with acetone and recrystallized in MeOH to give the title compound (1.10 g, 20% yield). $^1$H NMR (400 MHz, DMSO-d$_6$) δ ppm 2.98 (s, 6 H), 3.79 (t, 2 H), 4.14 (t, 2 H).

Intermediate 6

7'-Bromo-3',4'-dihydro-1'H-spiro[cyclopropane-1,2'-naphthalene]-1'-one

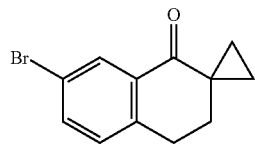 [SMILES: O=C1c2cc(Br)ccc2CCC12CC2]

To a solution of 7-bromo-1-tetralone (1.03 g, 4.58 mmol) in tert-butanol (10 mL) was added sodium iodide (0.131 g, 0.872 mmol) and sodium hydride (0.349 g, 60% suspension in mineral oil, 8.72 mmol). The reaction mixture was stirred at r.t. for 20 min. Then (2-chloroethyl)dimethylsulfonium iodide (Intermediate 5, 1.10 g, 4.36 mmol) was added portionwise over 1 h. After the reaction had reached completion, water (15 mL) was added and the resulting mixture was extracted with EtOAc (3×15 mL). The combined organic layers were dried with sodium sulfate, filtered and concentrated in vacuo. The product was purified by flash chromatography using 5% EtOAc in heptanes as eluent to give the title compound (0.789 g, 78%). $^1$H NMR (400 MHz, CDCl$_3$) δ ppm 0.84 (dd, 2 H), 1.40 (dd, 2 H), 1.95 (t, 2 H), 2.93 (t, 2 H), 7.14 (d, 1 H), 7.55 (dd, 1 H), 8.11 (d, 1 H); MS (ES+) m/z 250.98, 253.03 [M+H]$^+$.

Intermediate 7

7'-Bromo-3',4'-dihydro-1'H-spiro[cyclohexane-1,2'-naphthalene]-1',4-dione

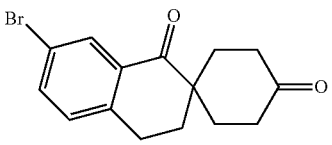 [SMILES: O=C1CCC2(CC1)CCc1ccc(Br)cc1C2=O]

7-Bromo-3,4-dihydronaphthalen-1-(2H)-one (10.3 g, 45.8 mmol) and methyl acrylate (9.08 mL, 101 mmol) was dissolved in THF (55 mL) and cooled in an ice bath. Potassium tert-butoxide (6.16 g, 54.9 mmol) was added in portions. The mixture was stirred for 1.5 h at r.t. Water (80 mL) and potassium hydroxide (2.57 g, 45.8 mmol) were added and the mixture was heated to 75° C. overnight in an open system. The mixture was cooled to r.t. and filtered. The obtained solid was dried in vacuo yielding the title compound (11.5 g, 82% yield): $^1$H NMR (CDCl$_3$) δ ppm 1.74-1.87 (m, 2 H), 2.15 (t, 2 H), 2.24-2.43 (m, 4 H), 2.62-2.72 (m, 2 H), 3.00 (t, 2 H), 7.16 (d, 1 H), 7.61 (dd, 1 H), 8.16 (d, 1 H); MS (ES+) m/z 307, 309 [M+H]$^+$.

Intermediate 8

7'-Bromo-4-hydroxy-3',4'-dihydro-1'H-spiro[cyclohexane-1,2'-naphthalen]-1'-one

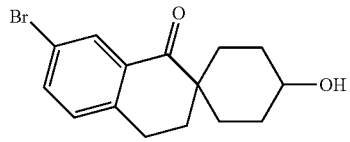 [SMILES: O=C1c2cc(Br)ccc2CCC12CCC(O)CC2]

7'-Bromo-3',4'-dihydro-1'H-spiro[cyclohexane-1,2'-naphthalene]-1',4-dione (Intermediate 7, 1.0 g, 3.26 mmol) was dissolved in THF (10 mL). The mixture was cooled to −78° C. Sodium borohydride (0.052 g, 1.37 mmol) was added and the mixture was stirred for 15 min at −78° C. Water (10 mL) was added and the reaction was allowed to attain r.t. slowly. EtOAc was added and the organic phase was separated, dried with MgSO$_4$ and concentrated in vacuo yielding the title compound (0.90 g, 89% yield). MS (ES+) m/z 309, 311 [M+H]$^+$.

Intermediate 9

7'-Bromo-4-methoxy-3',4'-dihydro-1'H-spiro[cyclohexane-1,2'-naphthalen]-1'-one

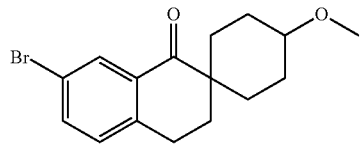 [SMILES: COC1CCC2(CCc3ccc(Br)cc3C2=O)CC1]

7'-Bromo-4-hydroxy-3',4'-dihydro-1'H-spiro[cyclohexane-1,2'-naphthalen]-1'-one (Intermediate 8, 1.78 g, 5.76 mmol) was dissolved in 2-methyl THF (15 mL) under an inert atmosphere and the solution was cooled to 0° C. Methyl iodide (0.720 mL, 11.5 mmol) was added followed by portion wise addition of potassium tert-butoxide (1.29 g, 11.5 mmol). The resulting mixture was stirred at r.t. overnight. Potassium tert-butoxide (0.323 g, 2.88 mmol) and methyl iodide (0.717 mL, 11.5 mmol) were added. The mixture was stirred for 1.5 h. Potassium tert-butoxide (0.194 g, 1.73 mmol) was added and the mixture was stirred for an additional 2 h. Brine was added and the phases were separated. The aqueous phase was extracted with EtOAc and to the combined organics were added activated charcoal. The mixture was filtered through a pad of diatomaceous earth and rinsed with EtOAc. The organic phase was concentrated in vacuo to give the title compound (1.41 g, 76% yield): MS (ES+) m/z 323 [M+H]⁺.

Intermediate 10

N-(7'-Bromo-3',4'-dihydro-1'H-spiro[cyclopropane-1,2'-naphthalene]-1'-ylidene)-2-methylpropane-2-sulfinamide

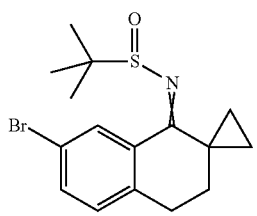 [SMILES: CC(C)(C)S(=O)N=C1c2cc(Br)ccc2CCC12CC2]

Titanium ethoxide (5.9 mL, 28.7 mmol), 2-methyl-2-propanesulfinamide (2.61 g, 21.5 mmol) and 7'-bromo-3',4'-dihydro-1'H-spiro[cyclopropane-1,2'-naphthalen]-1'-one (Intermediate 6, 3.6 g, 14.3 mmol) in dry 2-Me THF (80 mL) were heated to 100° C. to give an azeotrope. In total 100 mL 2-Me THF was removed and replaced by new 2-Me THF in 50 mL portions over a period of 4 h. The mixture was refluxed overnight. The azeotropic distillation was continued for 9 h and then more 2-methyl-2-propanesulfinamide (2.61 g, 21.5 mmol) and titanium ethoxide (5.9 mL, 28.7 mmol) were added. In total 90 mL 2-Me THF were removed and replaced by new 2-Me THF in 50 mL portions. The mixture was refluxed overnight and the azeotropic distillation was continued for 6 h. The cooled reaction mixture was added to a mixture of MeOH (105 mL), sat. aq. NaHCO₃ (41 mL) and EtOAc (430 mL). The resulting slurry was stirred for 2 h and was then filtered through a mixture of diatomaceous earth and Na₂SO₄ and concentrated. Some material crystallized from the mixture. The solid was triturated with EtOAc/n-heptane and collected by filtration. The mother liquor was purified by flash silica gel chromatography using CHCl₃/MeOH 50:1 as eluent and the obtained product was recrystallized from EtOAc/n-heptane. Combining the obtained solids gave 2.02 g (40% yield) of the title compound. ¹H NMR (500 MHz, DMSO-d₆) δ ppm 1.06 (d, 2 H), 1.14 (s, 9 H), 1.40 (d, 2 H), 1.64-1.84 (m, 2 H), 2.83 (m, 2H), 7.36 (d, 1 H), 7.69 (dd, 1 H), 8.16 (d, 1 H); MS (ES+) m/z 354.0 [M+H]⁺.

Intermediate 11

7'-Bromo-3',4'-dihydro-1'H-spiro[cyclopropane-1,2'-naphthalen]-1'-imine

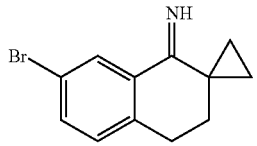 [SMILES: N=C1c2cc(Br)ccc2CCC12CC2]

HCl (4 M in 1,4-dioxane) (8.38 mL, 33.5 mmol) was added to a warm solution of N-(7'-bromo-3',4'-dihydro-1'H-spiro[cyclopropane-1,2'-naphthalene]-1'-ylidene)-2-methylpropane-2-sulfinamide (Intermediate 10, 1.19 g, 3.35 mmol) in dry dioxane (12 mL) under Ar (g). The mixture was stirred at r.t. for 40 min after which diethyl ether was added. The precipitate was filtered and washed with diethyl ether and then taken up in CH₂Cl₂ and washed twice with sat. aq. NaHCO₃. The organic phase was dried (Na₂SO₄), filtered and concentrated to give the title compound (0.717 g, 85% yield). MS (ES+) m/z 250.0 [M+H]⁺.

Intermediate 12

7'-Bromo-5''-methyl-3',4'-dihydrodispiro[cyclopropane-1,2'-naphthalene-1',2'''-imidazole]-4''(3''H)-thione

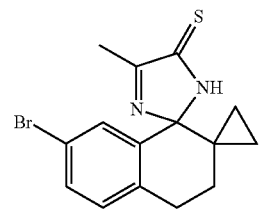 [SMILES: CC1=NC2(NC1=S)c1cc(Br)ccc1CCC21CC1]

7'-Bromo-3',4'-dihydro-1'H-spiro[cyclopropane-1,2'-naphthalen]-1'-imine (Intermediate 11, 717 mg, 2.87 mmol) and 2-oxopropanethioamide (970 mg, 9.40 mmol) were dissolved in dry MeOH (25 mL) and heated at 60° C. under argon for 24 h. After standing at r.t. overnight the formed precipitate was filtered and washed with MeOH. Drying in vacuo afforded the title compound (688 mg, 65% yield). ¹H NMR (500 MHz, DMSO-d₆) δ ppm 0.27-0.35 (m, 1 H), 0.35-0.45 (m, 2 H), 0.47-0.53 (m, 1 H), 1.69-1.79 (m, 1 H), 2.03-2.12 (m, 1 H), 2.27 (s, 3 H), 2.90 (t, 2 H), 6.73 (d, 1 H), 7.24 (d, 1 H), 7.47 (dd, 1 H), 12.28 (s, 1 H); MS (ES+) m/z 335.0 [M+H]⁺.

Intermediate 13

N-(7'-Bromo-4-methoxy-3',4'-dihydro-1'H-spiro[cyclohexane-1,2'-naphthalene]-1'-ylidene)-2-methylpropane-2-sulfinamide

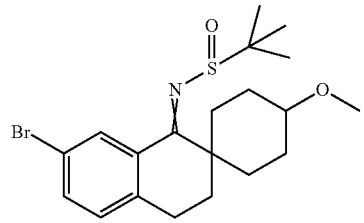 [SMILES: COC1CCC2(CCc3ccc(Br)cc3C2=NS(=O)C(C)(C)C)CC1]

7'-Bromo-4-methoxy-3',4'-dihydro-1'H-spiro[cyclohexane-1,2'-naphthalen]-1'-one (Intermediate 9, 2.26 g, 6.99 mmol), 2-methylpropane-2-sulfinamide (1.27 g, 10.5 mmol) and titanium ethoxide (2.88 mL, 14.0 mmol) were dissolved in 2-Me THF (15 mL) and heated to reflux over the weekend. The reaction was stopped and cooled to r.t. EtOAc (30 mL) and water (15 mL) were added under stirring. The mixture was then let to stand without stirring for 1 h. The organic phase was collected by filtration, dried using a phase separator and concentrated in vacuo. The product was purified by flash column chromatography using a gradient of 0-100% EtOAc in heptane to give the title compound (0.61 g, 20% yield): MS (ES+) m/z 426.11 [M+H]⁺.

Intermediate 14

7'-Bromo-4-methoxy-3',4'-dihydro-1'H-spiro[cyclohexane-1,2'-naphthalen]-1'-imine

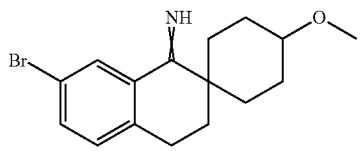 [SMILES: COC1CCC2(CCc3ccc(Br)cc3C2=N)CC1]

To N-(7'-bromo-4-methoxy-3',4'-dihydro-1'H-spiro[cyclohexane-1,2'-naphthalene]-1'-ylidene)-2-methylpropane-2-sulfinamide (Intermediate 13, 0.610 g, 1.43 mmol) under $N_2$ (g) was added HCl (4 M in 1,4-dioxane, 3.58 mL, 14.3 mmol). The mixture was stirred at r.t. for 45 min and was then concentrated. DCM (approx. 2 mL) was added followed by $Et_2O$. A solid formed and was filtered off and washed with $Et_2O$. The solid was dissolved in DCM. $NaHCO_3$ (sat. aq.) was added and the mixture was poured into a phase separator. The organic phase was collected and concentrated to give the title compound (0.35 g, 76% yield): MS (EI) m/z 321 $M^+$.

Intermediate 15

7'-Bromo-4-methoxy-5"-methyl-3',4'-dihydrodispiro[cyclohexane-1,2'-naphthalene-1',2"-imidazole]-4"(3"H)-thione

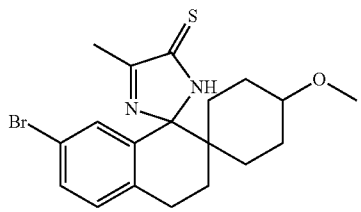 [SMILES: COC1CCC2(CCc3ccc(Br)cc3C23N=C(C)C(=S)N3)CC1]

7'-Bromo-4-methoxy-3',4'-dihydro-1'H-spiro[cyclohexane-1,2'-naphthalen]-1'-imine (Intermediate 14, 0.350 g, 1.09 mmol) and 2-oxopropanethioamide (Intermediate 1, 0.336 g, 3.26 mmol) were dissolved in dry MeOH (5 mL) and the resulting orange solution was heated at 60° C. under $N_2$ (g) overnight. The mixture was concentrated and purified by flash column chromatography using a gradient of 0-10% EtOAc in heptane to give the title compound (0.192 g, 43% yield): MS (ES+) m/z 407.12 $[M+H]^+$.

EXAMPLES

Example 1

7'-Bromo-5"-methyl-3',4'-dihydrodispiro[cyclopropane-1,2'-naphthalene-1',2"-imidazol]-4"-amine

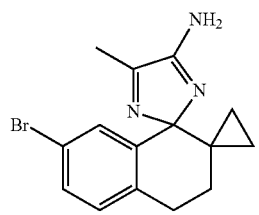 [SMILES: CC1=NC2(N=C1N)c1cc(Br)ccc1CCC21CC1]

7'-Bromo-5"-methyl-3',4'-dihydrodispiro[cyclopropane-1,2'-naphthalene-1',2"-imidazole]-4"(3"H)-thione (Intermediate 12, 0.688 g, 2.05 mmol) in ammonia (7 M in methanol, 18 mL, 126 mmol) was heated in a microwave reactor for 60 min at 100° C. Five times the mixture was concentrated, re-dissolved in ammonia (7 M in methanol, 18 mL, 126 mmol) and microwaved again for 40 to 60 minutes at 100° C. Purification by flash silica gel chromatography using a stepwise gradient of $CHCl_3$/MeOH (30:1-20:1-10:1) gave the title compound (0.532 g, 81% yield). $^1$H NMR (500 MHz, DMSO-$d_6$) δ ppm 0.00-0.08 (m, 1 H), 0.11 (ddd, 1 H), 0.22 (ddd, 1 H), 0.51 (dt, 1 H), 1.46 (dt, 1 H), 2.17 (s, 3 H), 2.28-2.39 (m, 1 H), 2.82-2.98 (m, 2 H), 6.56 (d, 1 H), 6.58 (br. s., 2 H), 7.12 (d, 1 H), 7.30 (dd, 1 H); MS (ES+) m/z 318.0 $[M+H]^+$.

Example 2

3-(4"-Amino-5"-methyl-3',4'-dihydrodispiro[cyclopropane-1,2'-naphthalene-1',2"-imidazol]-7'-yl)-5-fluorobenzonitrile

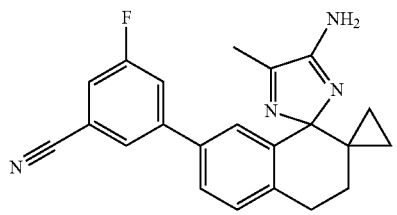 [SMILES: CC1=NC2(N=C1N)c1cc(-c3cc(F)cc(C#N)c3)ccc1CCC21CC1]

3-Cyano-5-fluorophenylboronic acid (83 mg, 0.50 mmol) was added to 7'-bromo-5"-methyl-3',4'-dihydrodispiro[cyclopropane-1,2'-naphthalene-1',2"-imidazol]-4"-amine (Example 1, 100 mg, 0.31 mmol) in dry 2-Me THF (2.85 mL), followed by aq. potassium carbonate (2.0 M, 0.471 mL, 0.94 mmol). Argon was bubbled through the mixture for one min. and then sodium tetrachloropalladate(II) (9.3 mg, 0.03 mmol) and 3-(di-tert-butylphosphonium)propane sulfonate (16.9 mg, 0.06 mmol) were added and the mixture was heated in a microwave reactor for 60 min at 100° C. Water, brine, 2-Me THF and EtOAc were added to the mixture and the phases were separated. The aqueous phase was extracted with EtOAc. The combined organic phases were washed with brine and water. The organic phase was dried ($Na_2SO_4$), filtered and concentrated. Recrystallization from MeOH and $CHCl_3$ and purification by preparative HPLC gave the title compound (96 mg, 85% yield).

$^1$H NMR (500 MHz, DMSO-$d_6$) δ ppm 0.03-0.17 (m, 2 H), 0.19-0.28 (m, 1 H), 0.49-0.59 (m, 1 H), 1.51 (dt, 1 H), 2.18 (s, 3 H), 2.33-2.44 (m, 1 H), 2.93-3.08 (m, 2 H), 6.52 (s, 2 H), 6.74 (d, 1 H), 7.29 (d, 1 H), 7.53 (dd, 1 H), 7.66 (d, 1 H), 7.74-7.84 (m, 2 H); MS (ES+) m/z 359.1 $[M+H]^+$.

Example 3

7'-(3,5-Difluorophenyl)-5"-methyl-3',4'-dihydrodispiro[cyclopropane-1,2'-naphthalene-1',2"-imidazol]-4"-amine The title compound was prepared following the procedure described for Example 2, starting from (3,5-difluorophenyl)boronic acid pinacol ester (113 mg, 0.47 mmol) and 7'-bromo-5"-methyl-3',4'-dihydrodispiro[cyclopropane-1,2'- naphthalene-1',2''-imidazol]-4''-amine (Example 1, 100 mg, 0.31 mmol). Purification by flash silica gel chromatography using a step wise gradient of $CHCl_3$/MeOH (40:1-30:1-20:1) and preparative HPLC gave the title compound (67 mg, 61% yield).

$^1$H NMR (500 MHz, DMSO-$d_6$) δ ppm 0.01-0.17 (m, 2 H), 0.24 (ddd, 1 H), 0.55 (dt, 1 H), 1.50 (dt, 1 H), 2.18 (s, 3 H), 2.33-2.44 (m, 1 H), 2.90-3.07 (m, 2 H), 6.52 (s, 2 H), 6.70 (d, 1 H), 7.10-7.22 (m, 3 H), 7.26 (d, 1 H), 7.48 (dd, 1 H); MS (ES+) m/z 352.1 [M+H]$^+$.

Example 4

7'-(5-Chloropyridin-3-yl)-5''-methyl-3',4'-dihydro-dispiro[cyclopropane-1,2'-naphthalene-1',2''-imidazol]-4''-amine

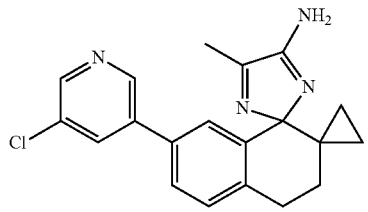 [SMILES: CC1=NC2(N=C1N)c1cc(-c3cncc(Cl)c3)ccc1CCC21CC1]

A mixture of 7'-bromo-5''-methyl-3',4'-dihydrodispiro[cyclopropane-1,2'-naphthalene-1',2''-imidazol]-4''-amine (Example 1, 100 mg, 0.31 mmol), 5-chloropyridin-3-ylboronic acid (74 mg, 0.47 mmol), [1,1'-bis(diphenylphosphino)ferrocene]palladium(II) chloride (23 mg, 0.03 mmol), aq. potassium carbonate (2 M, 0.31 mL, 0.63 mmol) and 1,4-dioxane (1 mL) were mixed in a vial and heated in a microwave reactor at 130° C. for 30 min. When cooled to r.t., the mixture was diluted with DCM, washed with water and dried over $Na_2SO_4$. The filtrate was concentrated and the product purified by preparative HPLC to give the title compound (41 mg, 37% yield). $^1$H NMR (500 MHz, DMSO-$d_6$) δ ppm 0.10 (m, 2 H), 0.24 (m, 1 H), 0.55 (m, 1 H), 1.51 (dt, 1 H), 2.18 (s, 3 H), 2.39 (m, 1 H), 3.01 (m, 2 H), 6.52 (br. s., 2 H), 6.74 (d, 1 H), 7.30 (d, 1 H), 7.52 (dd, 1 H), 7.97 (s, 1 H), 8.57 (d, 1 H), 8.61 (d, 1 H); MS (APCI+) m/z 351 [M+H]$^+$.

Example 5

7'-Bromo-4-methoxy-5''-methyl-3',4'-dihydrodispiro[cyclohexane-1,2'-naphthalene-1',2''-imidazol]-4''-amine (7'-Bromo-4-methoxy-5''-methyl-3',4'-dihydrodispiro[cyclohexane-1,2'-naphthalene-1',2''-imidazole]-4''(3''H)-thione (Intermediate 15, 0.191 g, 0.47 mmol) and ammonia (7M in MeOH, 2.5 mL, 17.5 mmol) were mixed in a microwave vial. The vial was sealed and the reaction was heated at 120° C. for 30 min in a microwave reactor. The mixture was concentrated and the residue was dissolved in ammonia (7M in MeOH, 2.5 mL, 17.5 mmol) and heated at 120° C. for 30 min in a microwave reactor. This was repeated six more times (8 runs in total). After evaporation of the solvent, the residue was partitioned between DCM and 2 M citric acid. The phases were separated and the organic layer was extracted with 2 M citric acid. The organic layer was discarded while the combined aqueous phases were basified to ~pH 12 by addition of 50% aq. NaOH. The aqueous phase was then extracted with EtOAc three times. The combined organic layers were dried using a phase separator and concentrated. The product was purified by preparative HPLC to give two isomers:

Isomer 1 (1r,4s)-7'-bromo-4-methoxy-5''-methyl-3',4'-dihydrodispiro[cyclohexane-1,2'-naphthalene-1',2''-imidazol]-4''-amine with retention time 15.81 min: (0.032 g, 17% yield)

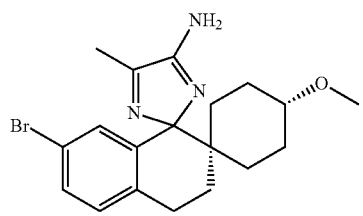

$^1$H NMR (500 MHz, DMSO-$d_6$) δ ppm 1.02-1.08 (m, 1 H) 1.09-1.26 (m, 3H) 1.35 (d, 2H) 1.70-1.78 (m, 2 H) 2.06-2.11 (m, 2 H) 2.18 (s, 3 H) 2.76-2.86 (m, 2 H) 2.86-2.93 (m, 1 H) 3.18 (s, 3 H) 6.57 (s, 2 H) 6.63 (d, 1 H) 7.09 (d, 1 H) 7.27 (dd, 1 H); MS (ES+) m/z 390.17 [M+H]$^+$.

Isomer 2 (1s,4r)-7'-bromo-4-methoxy-5''-methyl-3',4'-dihydrodispiro[cyclohexane-1,2'-naphthalene-1',2''-imidazol]-4''-amine with retention time 17.65 min (0.016 g, 8% yield)

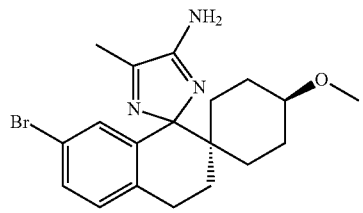

$^1$H NMR (500 MHz, DMSO-$d_6$) δ ppm 0.71 (d, 1 H) 1.05 (d, 1 H) 1.34 (td, 1 H) 1.41-1.51 (m, 2 H) 1.55-1.67 (m, 3 H) 2.09 (t, 2 H) 2.17 (s, 3 H) 2.76-2.90 (m, 2 H) 3.11 (s, 3 H) 3.26-3.30 (m, 1 H) 6.58 (br. s., 2 H) 6.64 (d, 1 H) 7.09 (d, 1 H) 7.27 (dd, 1 H); MS (ES+) m/z 390.10 [M+H]$^+$.

Example 6

3-[4''-Amino-4-methoxy-5''-methyl-3',4'-dihydrodispiro[cyclohexane-1,2'-naphthalene-1',2''-imidazol]-7'-yl]-5-methoxybenzonitrile 7'-Bromo-4-methoxy-5''-methyl-3',4'-dihydrodispiro[cyclohexane-1,2'-naphthalene-1',2''-imidazol]-4''-amine (Example 5, 0.184 g, 0.47 mmol), 3-methoxy-5-(4,4,5,5-tetramethyl-1,3,2-dioxaborolan-2-yl)benzonitrile (0.122 g, 0.47 mmol), 3-(di-tert-butylphosphonium)propane sulfonate (0.013 g, 0.05 mmol), sodium tetrachloropalladate(II) (6.95 mg, 0.02 mmol), 2-methyltetrahydrofuran (3 mL) and potassium carbonate (2.0 M, 0.708 mL, 1.42 mmol) were added to a microwave vial. The vial was sealed and heated with MW for 30 min at 130° C. The same amount of ligand and Pd-catalyst were added again and the reaction was heated in the MW for 15 min at 130° C. Water and 2-Me THF was added and the water phase was eliminated. The organic phase was washed once with brine and once with water. The organic phase was concentrated in vacuo. The product was purified using prep HPLC. Fractions containing the isomeric products were collected separately and the MeOH was evaporated.

DCM was added and the mixture was poured into a phase separator. The organic phase was concentrated in vacuo to give:

Isomer 1 3-[(1r,4s)-4''-amino-4-methoxy-5''-methyl-3',4'-dihydrodispiro[cyclohexane-1,2'-naphthalene-1',2''-imidazol]-7'-yl]-5-methoxybenzonitrile (0.038 g, 18% yield) (first eluting)

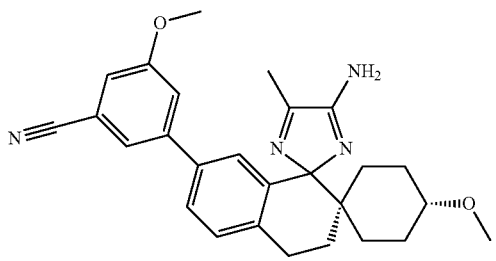

(500 MHz, DMSO-$d_6$) δ ppm 1.09 (br. s., 1 H), 1.00-1.32 (m, 4 H), 1.42 (d, 2 H), 1.76 (br. s., 2 H), 2.07-2.21 (m, 5 H), 2.84-2.99 (m, 3 H), 3.19 (s, 3 H), 3.85 (s, 3 H), 6.53 (s, 2 H), 6.77 (s, 1 H), 7.22-7.27 (m, 2 H), 7.38-7.41 (m, 1 H), 7.43 (s, 1 H), 7.45-7.49 (m, 1 H); MS (MM-ES+APCI)+m/z 443 [M+H]$^+$.

Isomer 2 3-[(1s,4r)-4''-amino-4-methoxy-5''-methyl-3',4'-dihydrodispiro[cyclohexane-1,2'-naphthalene-1',2''-imidazol]-7'-yl]-5-methoxybenzonitrile (0.034 g, 16% yield) (second eluting)

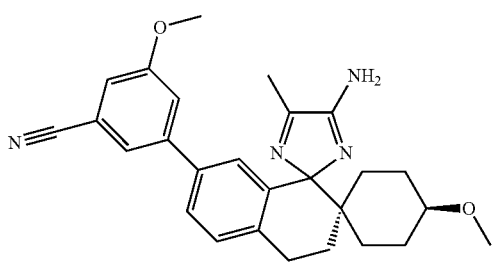

$^1$H NMR (500 MHz, DMSO-$d_6$) δ ppm 0.74 (d, 1 H), 1.12 (d, 1 H), 1.31-1.43 (m, 1 H), 1.43-1.55 (m, 2 H), 1.59 (br. s., 1 H), 1.61-1.74 (m, 2 H), 2.10-2.20 (m, 5 H), 2.84-3.01 (m, 2 H), 3.12 (s, 3 H), 3.30 (br. s., 1 H), 3.85 (s, 3 H), 6.53 (br. s., 2 H), 6.78 (s, 1 H), 7.21-7.25 (m, 2 H), 7.39 (s, 1 H), 7.43 (s, 1 H), 7.46 (dd, 1 H); MS (MM-ES+APCI)+m/z 443 [M+H]$^+$.

Example 7

7'-(5-Chloropyridin-3-yl)-4-methoxy-5''-methyl-3',4'-dihydrodispiro[cyclohexane-1,2'-naphthalene-1',2''-imidazol]-4''-amine 7'-Bromo-4-methoxy-5''-methyl-3',4'-dihydrodispiro[cyclohexane-1,2'-naphthalene-1',2''-imidazol]-4''-amine (Example 5, 0.2 g, 0.51 mmol), 3-chloro-5-(4,4,5,5-tetramethyl-1,3,2-dioxaborolan-2-yl)pyridine (123 mg, 0.51 mmol), 3-(di-tert-butylphosphonium)propane sulfonate (0.014 g, 0.05 mmol), sodium tetrachloropalladate(II) (7.54 mg, 0.03 mmol), 2-methyltetrahydrofuran (3 mL) and aq. potassium carbonate (2.0 M, 0.769 mL, 1.54 mmol) were added to microwave vial. The vial was sealed and heated in the MW for 30 min at 130° C. The same amount of ligand and Pd-catalyst were added again and the reaction was heated in the MW for 15 min at 130° C. This procedure was repeated twice more. Water and 2-Me THF were added. The water phase was eliminated and the organic phase was washed once with brine and water. The organic phase was concentrated in vacuo. The product was purified using prep HPLC to give:

Isomer 1 (1r,4s)-7'-(5-chloropyridin-3-yl)-4-methoxy-5''-methyl-3',4'-dihydrodispiro[cyclohexane-1,2'-naphthalene-1',2''-imidazol]-4''-amine (first eluting, 10.5 mg, 5% yield) after one additional purification by preparative HPLC

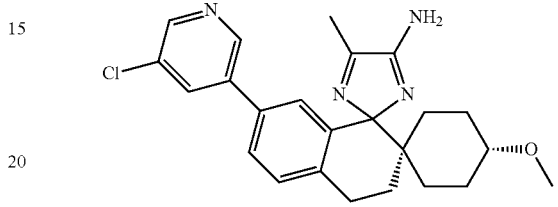

$^1$H NMR (500 MHz, CD$_3$OD) δ ppm 1.25-1.47 (m, 5 H), 1.63 (d, 1 H), 1.88 (t, 2 H), 2.16-2.29 (m, 2 H), 2.32 (s, 3 H), 2.96-3.14 (m, 3 H), 3.33 (s, 3 H), 6.90 (s, 1 H), 7.35 (d, 1 H), 7.49 (d, 1 H), 7.98 (s, 1 H), 8.48 (s, 1 H), 8.58 (s, 1 H); MS (MM-ES+APCI)+ m/z 423 [M+H]$^+$.

Isomer 2 (1s,4r)-7'-(5-chloropyridin-3-yl)-4-methoxy-5''-methyl-3',4'-dihydrodispiro[cyclohexane-1,2'-naphthalene-1',2''-imidazol]-4''-amine (second eluting, 10 mg, 5% yield)

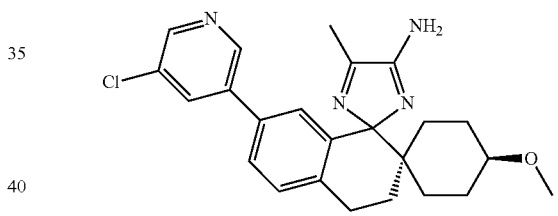

$^1$H NMR (500 MHz, DMSO-$d_6$) δ ppm 0.75 (d, 1 H), 1.11 (d, 1 H), 1.33-1.56 (m, 3 H), 1.56-1.74 (m, 3 H), 2.07-2.21 (m, 5 H), 2.82-3.03 (m, 2 H), 3.12 (s, 3 H), 3.30 (br. s., 1 H), 6.52 (br. s., 2 H), 6.81 (s, 1 H), 7.26 (d, 1 H), 7.50 (d, 1 H), 7.96 (s, 1 H), 8.60 (s, 1 H), 8.57 (s, 1 H); MS (MM-ES+APCI)+ m/z 423 [M+H]$^+$.

Example 8

4-Methoxy-5''-methyl-7'-[5-(prop-1-yn-1-yl)pyridin-3-yl]-3',4'-dihydrodispiro[cyclohexane-1,2'-naphthalene-1',2''-imidazol]-4''-amine 7'-Bromo-4-methoxy-5''-methyl-3',4'-dihydrodispiro[cyclohexane-1,2'-naphthalene-1',2''-imidazol]-4''-amine (Example 5, 110 mg, 0.28 mmol) and 5-(prop-1-ynyl)pyridin-3-ylboronic acid (Intermediate 3, 50 mg, 0.31 mmol) were dissolved in 2-Me THF (2 mL). To the solution was added degassed aq. potassium carbonate (2 M, 0.423 mL, 0.85 mmol). The resulting solution was degassed by Ar (g), and then sodium tetrachloropalladate(II) (4.2 mg, 0.01 mmol) and 3-(di-tert-butylphosphonium)propane sulfonate (7.6 mg, 0.03 mmol) were added. The vial was capped and heated in MW at 100° C. until all starting material had been consumed. The mixture was cooled to r.t. Water and EtOAc were added.

The phases were separated and the aqueous phase was re-extracted with EtOAc twice. The combined organics were washed with brine, dried using a phase separator and concentrated. The residue was purified by reversed phase chromatography (XBridge™ Prep C8 10 μm OBD™ 19×250 mm column, a gradient of 45-80% B (100% MeOH) in A (0.2% NH$_3$ in MilliQ water) at a flow rate of 20 mL/min) to give Isomer 1 (1s,4r)-4-methoxy-5"-methyl-7'-[5-(prop-1-yn-1-yl)pyridin-3-yl]-3',4'-dihydrodispiro[cyclohexane-1,2'-naphthalene-1',2"-imidazol]-4"-amine (first eluting, 5.1 mg 4% yield)

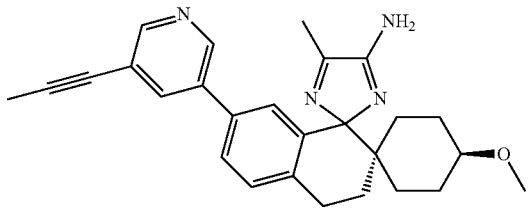

$^1$H NMR (500 MHz, DMSO-d$_6$) δ ppm 0.74 (d, 1 H) 1.12 (d, 1 H) 1.34-1.41 (m, 1 H) 1.43-1.54 (m, 2 H) 1.57-1.74 (m, 3 H) 2.10 (s, 3 H) 2.14 (t, 2 H) 2.17 (s, 3 H) 2.86-2.99 (m, 2 H) 3.12 (s, 3 H) 3.30 (d, 1 H) 6.53 (s, 2 H) 6.79 (d, 1 H) 7.25 (d, 1 H) 7.46 (dd, 1 H) 7.79 (t, 1 H) 8.52 (d, 1 H) 8.57 (d, 1 H); MS (ES+) m/z 427.26 [M+H]$^+$.

Isomer 2 (1r,4s)-4-methoxy-5"-methyl-7'-[5-(prop-1-yn-1-yl)pyridin-3-yl]-3',4'-dihydrodispiro[cyclohexane-1,2'-naphthalene-1',2"-imidazol]-4"-amine (second eluting, 6.5 mg 5% yield)

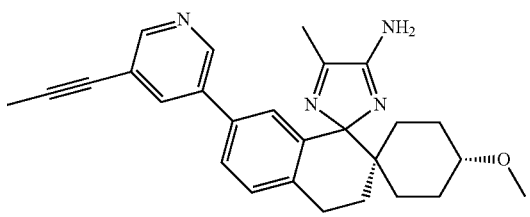

$^1$H NMR (500 MHz, DMSO-d$_6$) δ ppm 1.05-1.11 (m, 1 H) 1.11-1.28 (m, 3 H) 1.43 (d, 2 H) 1.72-1.80 (m, 2 H) 2.10 (s, 3 H) 2.11-2.17 (m, 2 H) 2.18 (s, 3 H) 2.85-3.00 (m, 3 H) 3.19 (s, 3 H) 6.53 (s, 2 H) 6.78 (d, 1 H) 7.25 (d, 1 H) 7.47 (dd, 1 H) 7.80 (t, 1 H) 8.51 (d, 1 H) 8.57 (d, 1 H); MS (ES+) m/z 427.26 [M+H]$^+$.

Example 9

3-(4"-Amino-5"-methyl-3',4'-dihydrodispiro[cyclopropane-1,2'-naphthalene-1',2"-imidazol]-7'-yl)-5-chlorobenzonitrile

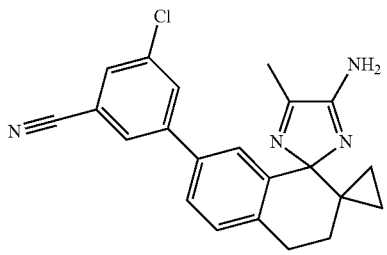 [SMILES: CC1=NC2(N=C1N)c1cc(-c3cc(Cl)cc(C#N)c3)ccc1CCC21CC1]

The title compound was prepared following the procedure described for Example 2, starting from 3-chloro-5-(4,4,5,5-tetramethyl-1,3,2-dioxaborolan-2-yl)benzonitrile (Intermediate 4, 71 mg, 0.27 mmol) and 7'-bromo-5"-methyl-3',4'-dihydrodispiro[cyclopropane-1,2'-naphthalene-1',2"-imidazol]-4"-amine (Example 1, 86 mg, 0.27 mmol). The product was purified by preparative HPLC to give the title compound (24 mg, 24% yield). $^1$H NMR (500 MHz, DMSO-d$_6$) δ ppm 0.08 (td, 1 H), 0.10-0.16 (m, 1 H), 0.24 (ddd, 1 H), 0.49-0.62 (m, 1 H), 1.49 (dt, 1 H), 2.18 (s, 3 H), 2.32-2.44 (m, 1 H), 2.94-3.07 (m, 2 H), 6.53 (br. s, 2 H), 6.73 (d, 1 H), 7.29 (d, 1 H), 7.52 (dd, 1 H), 7.79 (t, 1 H), 7.88 (s, 1 H), 7.98 (t, 1 H); MS (ES+) m/z 375 [M+H]$^+$.

Example 10

3-(4"-Amino-4-methoxy-5"-methyl-3',4'-dihydrodispiro[cyclohexane-1,2'-naphthalene-1',2"-imidazol]-7'-yl)-5-chlorobenzonitrile

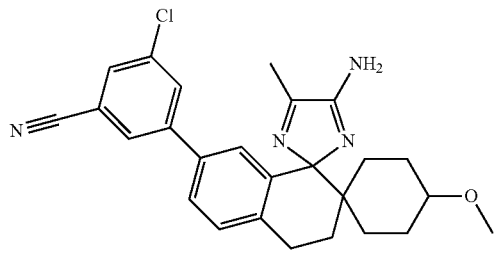 [SMILES: COC1CCC2(CCc3ccc(-c4cc(Cl)cc(C#N)c4)cc3C23N=C(C)C(N)=N3)CC1]

The title compound was prepared following the procedure described for Example 2, starting from 7'-bromo-4-methoxy-5"-methyl-3',4'-dihydrodispiro[cyclohexane-1,2'-naphthalene-1',2"-imidazol]-4"-amine (Example 5, 125 mg, 0.32 mmol) and 3-chloro-5-(4,4,5,5-tetramethyl-1,3,2-dioxaborolan-2-yl)benzonitrile (Intermediate 4, 93 mg, 0.35 mmol). The product was purified using preparative chromatography followed by concentration of the fractions, extraction of the remaining aqueous phase with DCM, washing the organic layer with water and concentration and drying in vacuo at 50° C. for 2 days to give:

Isomer 1: 3-[(1r,4s)-4"-amino-4-methoxy-5"-methyl-3',4'-dihydrodispiro[cyclohexane-1,2'-naphthalene-1',2"-imidazol]-7'-yl]-5-chlorobenzonitrile with retention time 11.9 min (38 mg, 27% yield)

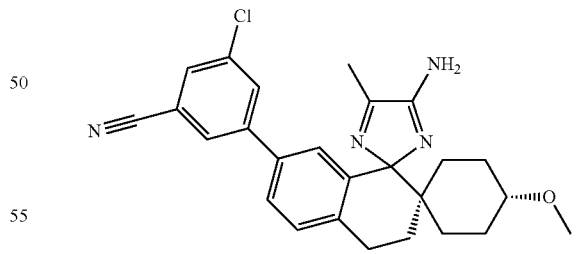

$^1$H NMR (500 MHz, DMSO-d$_6$) δ 1.01-1.29 (m, 4 H), 1.41 (d, 2 H), 1.76 (dd, 2 H), 2.07-2.17 (m, 2H), 2.19 (s, 3H), 2.86-3.01 (m, 3 H), 3.19 (s, 3 H), 6.55 (s, 2 H), 6.81 (d, 1 H), 7.26 (d, 1 H), 7.51 (dd, 1 H), 7.80 (t, 1 H), 7.85-7.90 (m, 1 H), 7.97 (t, 1 H); MS (ES+) m/z 447 [M+H]$^+$.

Isomer 2: 3-[(1s,4r)-4"-amino-4-methoxy-5"-methyl-3',4'-dihydrodispiro[cyclohexane-1,2'-naphthalene-1',2"-imidazol]-7'-yl]-5-chlorobenzonitrile with retention time 13.5 (31 mg, 22% yield)

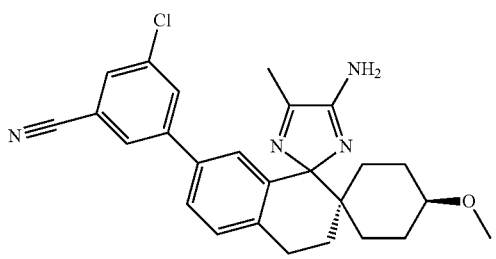

¹H NMR (500 MHz, DMSO-d₆) δ 0.68-0.77 (m, 1 H), 1.06-1.13 (m, 1 H), 1.32-1.54 (m, 4 H), 1.57-1.74 (m, 3 H), 2.14 (t, 2 H), 2.17 (s, 3 H), 2.86-3.01 (m, 2 H), 3.12 (s, 3 H), 3.30 (br. s., 1 H), 6.54 (br. s., 2 H), 6.81 (d, 1 H), 7.26 (d, 1 H), 7.50 (dd, 1 H), 7.79 (t, 1 H), 7.87 (s, 1 H), 7.98 (d, 1 H). MS (ES+) m/z 447 [M+H]⁺.

Example 11

Separation of the enantiomers of 3-[(1r,4s)-4"-amino-4-methoxy-5"-methyl-3',4'-dihydrodispiro[cyclohexane-1,2'-naphthalene-1',2"-imidazol]-7'-yl]-5-chlorobenzonitrile The enantiomers of 3-[(1r,4s)-4"-amino-4-methoxy-5"-methyl-3',4'-dihydrodispiro[cyclohexane-1,2'-naphthalene-1',2"-imidazol]-7'-yl]-5-chlorobenzonitrile (Example 11, isomer 1, 27 mg, 0.06 mmol) were separated using a SFC Berger Multigram II system equipped with a Chiracel OD-H (20*250 mm; 5 μm) column, and a mobile phase consisting of 25% MeOH (containing 0.1% DEA) and 75% CO₂ at a flow rate of 50 mL/min to give:
Isomer 1: 3-[(1r,4s)-4"-amino-4-methoxy-5"-methyl-3',4'-dihydrodispiro[cyclohexane-1,2'-naphthalene-1',2"-imidazol]-7'-yl]-5-chlorobenzonitrile with retention time 3.4 min (12 mg, 43% yield)

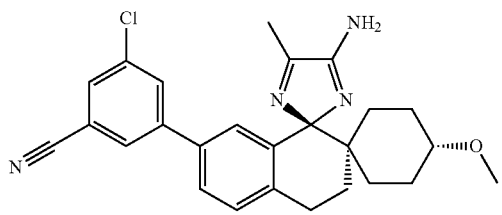 [SMILES: CO[C@H]1CC[C@@]2(CCc3ccc(-c4cc(Cl)cc(C#N)c4)cc3[C@@]23N=C(C)C(N)=N3)CC1]

¹H NMR (500 MHz, DMSO-d₆) δ ppm 1.20 (m, 4 H) 1.41 (d, 2 H) 1.76 (m, 2 H) 2.13 (m, 2 H) 2.19 (s, 3 H) 2.93 (m, 3 H) 3.19 (s, 3 H) 6.54 (s, 2 H) 6.81 (d, 1 H) 7.26 (d, 1 H) 7.51 (dd, 1 H) 7.80 (t, 1 H) 7.88 (t, 1 H) 7.97 (t, 1 H); MS (APCI+) m/z 447 [M+H]⁺.
Isomer 2: 3-[(1r,4s)-4"-amino-4-methoxy-5"-methyl-3',4'-dihydrodispiro[cyclohexane-1,2'-naphthalene-1',2"-imidazol]-7'-yl]-5-chlorobenzonitrile with retention time 7.8 min. (12 mg, 44% yield)

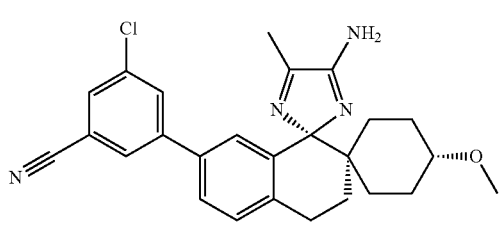 [SMILES: CO[C@H]1CC[C@@]2(CCc3ccc(-c4cc(Cl)cc(C#N)c4)cc3[C@]23N=C(C)C(N)=N3)CC1]

¹H NMR (500 MHz, DMSO-d₆) δ ppm 1.23 (br. s., 4 H) 1.41 (d, 2 H) 1.76 (m, 2 H) 2.13 (d, 2 H) 2.18 (s, 3 H) 2.93 (m, 3 H) 3.19 (s, 3 H) 6.54 (s, 2H) 6.81 (d, 1 H) 7.26 (d, 1 H) 7.51 (dd, 1 H) 7.80 (t, 1 H) 7.88 (t, 1 H) 7.97 (m, 1 H); MS (APCI+) m/z 447 [M+H]⁺.

BIOLOGICAL ASSAYS

The level of activity of the compounds was tested using the following methods:
TR-FRET Assay
The β-secretase enzyme used in the TR-FRET is prepared as follows:
The cDNA for the soluble part of the human β-Secretase (AA 1-AA 460) was cloned using the ASP2-Fc10-1-IRES-GFP-neoK mammalian expression vector. The gene was fused to the Fc domain of IgG1 (affinity tag) and stably cloned into HEK 293 cells. Purified sBACE-Fc was stored in −80° C. in 50 mM Glycine pH 2.5, adjusted to pH 7.4 with 1 M Tris and had a purity of 40%.
The enzyme (truncated form) was diluted to 6 μg/mL (stock 1.3 mg/mL) and the TruPoint BACE1 Substrate to 200 nM (stock 120 μM) in reaction buffer (NaAcetate, chaps, triton x-100, EDTA pH4.5). Enzyme and compound in dimethylsulphoxide (final DMSO concentration 5%) was mixed and pre-incubated for 10 minutes at RT. Substrate was then added and the reaction was incubated for 15 minutes at RT. The reaction was stopped with the addition of 0.35 vol Stop solution (NaAcetate, pH 9). The fluorescence of the product was measured on a Victor II plate reader with excitation wavelengths of 340-485 nm and emission wavelengths of 590-615 nm. The final concentration of the enzyme was 2.7 μg/ml; the final concentration of substrate was 100 nM (Km of ~250 nM). The dimethylsulphoxide control, instead of test compound, defined the 100% activity level and 0% activity was defined by wells lacking enzyme (replaced with reaction buffer) or by a saturating dose of a known inhibitor, 2-amino-6-[3-(3-methoxyphenyl)phenyl]-3,6-dimethyl-5H-pyrimidin-4-one. A control inhibitor was also used in dose response assays and had an IC50 of ~150 nM.
Diluted TR-FRET Assay
Compounds with a high affinity were further tested in a diluted TR-FRET assay, conditions as described above for the TR-FRET assay, but with 50 times less enzyme and a 6.5 h long reaction time at r.t. in the dark.
sAPPβ Release Assay
SH-SY5Y cells were cultured in DMEM/F-12 with Glutamax, 10% FCS and 1% non-essential amino acids and cryopreserved and stored at −140° C. at a concentration of 7.5-9.5×10⁶ cells per vial. Thaw cells and seed at a conc. of around 10000 cells/well in DMEM/F-12 with Glutamax, 10% FCS and 1% non-essential amino acids to a 384-well tissue culture treated plate, 100 μL cell susp/well. The cell plates were then incubated for 7-24 h at 37° C., 5% CO₂. The cell medium was removed, followed by addition of 30 μL compound diluted in DMEM/F-12 with Glutamax, 10% FCS, 1% non-essential amino acids and 1% PeSt to a final conc. of 1% DMSO. The compounds were incubated with the cells for 17 h (overnight) at 37° C., 5% CO₂. Meso Scale Discovery (MSD) plates were used for the detection of sAPPβ release. MSD sAPPβ plates were blocked in 1% BSA in Tris wash buffer (40 μL/well) for 1 h on shake at r.t. and washed 1 time in Tris wash buffer (40 μL/well). 20 μL of medium was transferred to the pre-blocked and washed MSD sAPPβ microplates, and the cell plates were further used in an ATP assay to measure cytotoxicity. The MSD plates were incubated with shaking at r.t. for 2 h and the media discarded. 10 μL detection antibody was added (1 nM) per well followed by incubation with shaking at r.t. for 2 h and then discarded. 40 μL Read Buffer was added per well and the plates were read in a SECTOR Imager.

ATP Assay

As indicated in the sAPPβ release assay, after transferring 20 μL medium from the cell plates for sAPPβ detection, the plates were used to analyse cytotoxicity using the ViaLight™ Plus cell proliferation/cytotoxicity kit from Cambrex BioScience that measures total cellular ATP. The assay was performed according to the manufacture's protocol. Briefly, 10 μL cell lysis reagent was added per well. The plates were incubated at r.t. for 10 min. Two min after addition of 25 μL reconstituted ViaLight™ Plus ATP reagent, the luminescence was measured. Tox threshold is a signal below 75% of the control.

Results

Typical $IC_{50}$ values for the compounds of the present invention are in the range of about 0.1 to about 100,000 nM. Biological data on particular example compounds is given below in Table 1.

TABLE 1

| Example | $IC_{50}$ in TR-FRET assay (nM) | $IC_{50}$ in sAPPβ release assay (nM) | Example | $IC_{50}$ in TR-FRET assay (nM) | $IC_{50}$ in sAPPβ release assay (nM) |
|---|---|---|---|---|---|
| 1 | 4870 | not tested | 2 | 79 | 23 |
| 3 | 130 | 118 | 4 | 30[a] | 11 |
| 5, isomer 1 | 411 | 78 | 5, isomer 2 | 8920 | not tested |
| 6, isomer 1 | 5.0[a] | 1.0 | 6, isomer 2 | 587 | 80 |
| 7, isomer 1 | 14[a] | 2.5 | 7, isomer 2 | 333 | 19 |
| 8, isomer 1 | 212 | 81 | 8, isomer 2 | 19 | 2.4 |
| 9 | 15[a] | 16 | 10, isomer 1 | 5.7[a] | 3.1 |
| 10, isomer 2 | 392 | 92 | 11, isomer 1 | 3.6[a] | 4.5 |
| 11, isomer 2 | >5000 | not tested | | | |

[a]$IC_{50}$ from the diluted FRET assay.

The invention claimed is:

1. A compound according to formula (I):

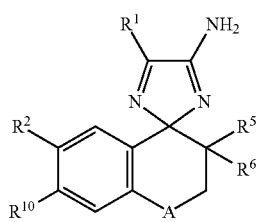

wherein

A is —O— or —CH$_2$—;

$R^1$ is $C_{1-6}$alkyl or $C_{1-6}$haloalkyl;

$R^2$ is hydrogen, $C_{0-6}$alkylaryl, $C_{0-6}$alkylheteroaryl, $C_{2-6}$alkynyl, $C_{2-6}$alkenyl, $C_{1-6}$alkyl, halogen, cyano, $C_{1-6}$haloalkyl, NHC(O)$R^9$ or OR$^8$, wherein said $C_{0-6}$alkylaryl, $C_{0-6}$alkylheteroaryl, $C_{2-6}$alkynyl, $C_{2-6}$alkenyl, $C_{1-6}$alkyl or $C_{1-6}$haloalkyl is optionally substituted with one to three $R^7$;

$R^5$ and $R^6$ are independently heterocyclyl, $C_{3-6}$cycloalkyl, aryl, heteroaryl or $C_{1-6}$alkyl, wherein said heterocyclyl, $C_{3-6}$cycloalkyl, aryl, heteroaryl or $C_{1-6}$alkyl is optionally substituted with one or two substituents independently selected from halogen, $C_{1-6}$alkyl, $C_{1-6}$haloalkyl, cyano or OR$^8$;

or $R^5$ and $R^6$ together with the carbon to which they are attached, form a ring B, which is a 3-14 membered cycloalkyl or heterocyclyl monocyclic ring, or a 9-14 membered bicyclic cycloalkyl or heterocyclyl ring; and wherein ring B is optionally substituted by one or two substituents independently selected from oxo, halogen, $C_{1-6}$alkyl, $C_{1-6}$haloalkyl, cyano, or OR$^8$; and ring B is optionally fused with an aryl or heteroaryl to form a bi- or polycyclic system;

$R^7$ is independently $C_{1-6}$alkyl, halogen, cyano, $C_{0-6}$alkyl$C_{3-6}$cycloalkyl, $C_{1-6}$haloalkyl, OC$_{1-6}$alkyl, OC$_{1-6}$haloalkyl, $C_{2-6}$alkynyl or $C_{2-6}$alkenyl, wherein said $C_{1-6}$alkyl, $C_{0-6}$alkyl$C_{3-6}$cycloalkyl, $C_{1-6}$haloalkyl, OC$_{1-6}$alkyl, OC$_{1-6}$haloalkyl, $C_{2-6}$alkynyl or $C_{2-6}$alkenyl is optionally substituted with 1-3 substituents independently selected from halogen, cyano, $C_{1-6}$alkyl, $C_{3-6}$cycloalkyl, $C_{3-6}$halocycloalkyl, $C_{1-6}$haloalkyl, OC$_{1-6}$alkyl and OC$_{1-6}$haloalkyl;

$R^8$ is independently hydrogen, $C_{1-6}$alkyl, $C_{2-6}$alkynyl, $C_{1-6}$haloalkyl, aryl or heteroaryl, wherein said $C_{1-6}$alkyl, $C_{1-6}$haloalkyl, aryl or heteroaryl is optionally substituted with a group selected from halogen, cyano, $C_{3-6}$cycloalkyl, $C_{3-6}$halocycloalkyl, OC$_{1-6}$alkyl and $C_{1-6}$alkyl;

$R^9$ is a heteroaryl, wherein said heteroaryl is optionally substituted with halogen, cyano, OR$^8$, $C_{1-6}$haloalkyl or $C_{1-6}$alkyl;

$R^{10}$ is hydrogen, halogen or methyl;

as a free base or a pharmaceutically acceptable salt thereof.

2. A compound according to claim 1, or a pharmaceutically acceptable salt thereof, wherein $R^1$ is $C_{1-3}$alkyl.

3. A compound according to claim 2, or a pharmaceutically acceptable salt thereof, wherein $R^1$ is methyl or ethyl.

4. A compound according to claim 1, or a pharmaceutically acceptable salt thereof, wherein $R^2$ is aryl, heteroaryl, $C_{2-6}$alkynyl, halogen, NHC(O)$R^9$ or OR$^8$, wherein said aryl, heteroaryl, or $C_{2-6}$alkynyl is optionally substituted with one to three $R^7$.

5. A compound according to claim 1, or a pharmaceutically acceptable salt thereof, wherein $R^5$ and $R^6$ are independently $C_{3-6}$cycloalkyl or heterocyclyl wherein said $C_{3-6}$cycloalkyl or heterocyclyl is optionally substituted with one or two substituents independently selected from $C_{1-6}$alkyl or OR$^8$.

6. A compound according to claim 1, or a pharmaceutically acceptable salt thereof, wherein $R^5$ and $R^6$ together with the carbon to which they are attached, form a ring B, which is a 3-14 membered cycloalkyl or heterocyclyl monocyclic ring; and wherein ring B is optionally substituted by one or two substituents independently selected from oxo, halogen, $C_{1-6}$alkyl or OR$^8$.

7. A compound according to claim 1, or a pharmaceutically acceptable salt thereof, wherein $R^5$ and $R^6$ together with the carbon to which they are attached form a cyclohexyl ring, which is substituted with OR$^8$.

8. A compound according to claim 1, or a pharmaceutically acceptable salt thereof, wherein $R^7$ is independently $C_{1-6}$alkyl, halogen, cyano, $C_{0-6}$alkyl$C_{3-6}$cycloalkyl, $C_{1-6}$haloalkyl, OC$_{1-6}$alkyl, OC$_{1-6}$haloalkyl, or $C_{2-6}$alkynyl, wherein said $C_{1-6}$alkyl, $C_{0-6}$alkyl$C_{3-6}$cycloalkyl, $C_{1-6}$haloalkyl, OC$_{1-6}$alkyl or $C_{2-6}$alkynyl is optionally substituted with 1-3 substituents independently selected from halogen, cyano, $C_{1-6}$alkyl, $C_{3-6}$cycloalkyl, $C_{3-6}$halocycloalkyl, $C_{1-6}$haloalkyl, OC$_{1-6}$alkyl and OC$_{1-6}$haloalkyl.

9. A compound according to claim 1, or a pharmaceutically acceptable salt thereof, wherein $R^7$ is independently halogen, cyano, OC$_{1-6}$alkyl or $C_{2-6}$alkynyl, wherein said $C_{2-6}$alkynyl or OC$_{1-6}$alkyl is optionally substituted with 1-3 substituents independently selected from $C_{1-6}$alkyl, $C_{3-6}$cycloalkyl, $C_{3-6}$halocycloalkyl or $C_{1-6}$haloalkyl.

10. A compound according to claim 1, or a pharmaceutically acceptable salt thereof, wherein $R^8$ is independently hydrogen, $C_{1-6}$alkyl or $C_{1-6}$haloalkyl.

11. A compound according to claim 1, or a pharmaceutically acceptable salt thereof, wherein A is —O— or —CH$_2$—;

$R^1$ is $C_{1-6}$alkyl;

$R^2$ is $C_{0-6}$alkylaryl, $C_{0-6}$alkylheteroaryl, $C_{2-6}$alkynyl, halogen, NHC(O)$R^9$ or $OR^8$; wherein said $C_{0-6}$alkylaryl, $C_{0-6}$alkylheteroaryl or $C_{2-6}$alkynyl is optionally substituted with one to three $R^7$;

$R^5$ and $R^6$ are independently $C_{3-6}$cycloalkyl or heterocyclyl, wherein said $C_{3-6}$cycloalkyl or heterocyclyl is optionally substituted with one or two substituents independently selected from halogen, $C_{1-6}$alkyl, $C_{1-6}$haloalkyl, cyano or $OR^8$;

or $R^5$ and $R^6$ together with the carbon to which they are attached, form a ring B, which is a 3-14 membered cycloalkyl or heterocyclyl monocyclic ring; and wherein ring B is optionally substituted by one or two substituents independently selected from oxo, halogen, $C_{1-6}$alkyl or $OR^8$;

$R^7$ is independently $C_{1-6}$alkyl, halogen, cyano, $C_{0-6}$alkyl$C_{3-6}$cycloalkyl, $C_{1-6}$haloalkyl, $OC_{1-6}$alkyl, $OC_{1-6}$haloalkyl, or $C_{2-6}$alkynyl, wherein said $C_{1-6}$alkyl, $C_{0-6}$alkyl$C_{3-6}$cycloalkyl, $C_{1-6}$haloalkyl, $OC_{1-6}$alkyl or $C_{2-6}$alkynyl, is optionally substituted with 1-3 substituents independently selected from halogen, cyano, $C_{1-6}$alkyl, $C_{3-6}$cycloalkyl, $C_{3-6}$halocycloalkyl, $C_{1-6}$haloalkyl, $OC_{1-6}$alkyl and $OC_{1-6}$haloalkyl;

$R^8$ is independently hydrogen, $C_{1-6}$alkyl, or $C_{1-6}$haloalkyl, wherein said $C_{1-6}$alkyl or $C_{1-6}$haloalkyl is optionally substituted with a group selected from halogen, cyano, $C_{3-6}$cycloalkyl, $C_{3-6}$halocycloalkyl, $OC_{1-6}$alkyl or $C_{1-6}$alkyl;

$R^9$ is heteroaryl, wherein said heteroaryl is optionally substituted with halogen, cyano, $OR^8$, $C_{1-6}$haloalkyl or $C_{1-6}$alkyl; and $R^{10}$ is hydrogen.

12. A compound according to claim 1, or a pharmaceutically acceptable salt thereof, wherein A is —O— or —CH$_2$—;

$R^1$ is $C_{1-3}$alkyl;

$R^2$ is aryl, heteroaryl, $C_{2-6}$alkynyl, halogen, NHC(O)$R^9$ or $OR^8$, wherein said aryl, heteroaryl or $C_{2-6}$alkynyl is optionally substituted with one to three $R^7$;

$R^5$ and $R^6$ are independently $C_{3-6}$cycloalkyl or heterocyclyl, wherein said $C_{3-6}$cycloalkyl or heterocyclyl is optionally substituted with one or two substituents independently selected from $C_{1-6}$alkyl or $OR^8$;

or $R^5$ and $R^6$ together with the carbon to which they are attached, form a ring B, which is a 3-14 membered cycloalkyl or heterocyclyl monocyclic ring; and wherein ring B is optionally substituted by one or two substituents independently selected from oxo, halogen, $C_{1-6}$alkyl or $OR^8$;

$R^7$ is independently $C_{1-6}$alkyl, halogen, cyano, $C_{0-6}$alkyl$C_{3-6}$cycloalkyl, $C_{1-6}$haloalkyl, $OC_{1-6}$alkyl, $OC_{1-6}$haloalkyl or $C_{2-6}$alkynyl, wherein said $C_{1-6}$alkyl, $C_{0-6}$alkyl$C_{3-6}$cycloalkyl, $C_{1-6}$haloalkyl, $OC_{1-6}$alkyl, $OC_{1-6}$haloalkyl or $C_{2-6}$alkynyl is optionally substituted with 1-3 substituents independently selected from halogen, cyano, $C_{1-6}$alkyl, $C_{3-6}$cycloalkyl, $C_{3-6}$halocycloalkyl, $C_{1-6}$haloalkyl, $OC_{1-6}$alkyl and $OC_{1-6}$haloalkyl;

$R^8$ is independently hydrogen, $C_{1-6}$alkyl or $C_{1-6}$haloalkyl, wherein said $C_{1-6}$alkyl or $C_{1-6}$haloalkyl is optionally substituted with a group selected from halogen, cyano, $C_{3-6}$cycloalkyl, $C_{3-6}$halocycloalkyl, $OC_{1-6}$alkyl or $C_{1-6}$alkyl;

$R^9$ is heteroaryl, wherein said heteroaryl is optionally substituted with halogen, cyano, $OR^8$, $C_{1-6}$haloalkyl or $C_{1-6}$alkyl; and $R^{10}$ is hydrogen.

13. A compound according to claim 1, selected from the group consisting of:

7'-Bromo-5"-methyl-3',4'-dihydrodispiro[cyclopropane-1,2'-naphthalene-1',2"-imidazol]-4"-amine;

3-(4"-Amino-5"-methyl-3',4'-dihydrodispiro[cyclopropane-1,2'-naphthalene-1',2"-imidazol]-7'-yl)-5-fuorobenzonitrile;

7'-(3,5-Difluorophenyl)-5"-methyl-3',4'-dihydrodispiro[cyclopropane-1,2'-naphthalene-1',2"-imidazol]-4"-amine;

7'-(5-Chloropyridin-3-yl)-5"-methyl-3',4'-dihydrodispiro[cyclopropane-1,2'-naphthalene-1',2"-imidazol]-4"-amine;

(1r,4s)-7'-Bromo-4-methoxy-5"-methyl-3',4'-dihydrodispiro[cyclohexane-1,2'-naphthalene-1',2"-imidazol]-4"-amine;

(1s,4r)-7'-Bromo-4-methoxy-5'-methyl-3',4'-dihydrodispiro[cyclohexane-1,2'-naphthalene-1',2"-imidazol]-4"-amine;

3-[(1r,4s)-4"-Amino-4-methoxy-5"-methyl-3',4'-dihydrodispiro[cyclohexane-1,2'-naphthalene-1',2"-imidazol]-7'-yl]-5-methoxybenzonitrile;

3-[(1s,4s)-4"-Amino-4-methoxy-5'-methyl-3',4'-dihydrodispiro[cyclohexane-1,2'-naphthalene-1',2"-imidazol]-7'-yl]-5-methoxybenzonitrile;

(1r,4s)-7'-(5-Chloropyridin-3-yl)-4-methoxy-5"-methyl-3',4'-dihydrodispiro[cyclohexane-1,2'-naphthalene-1', 2"-imidazol]-4"-amine;

(1s,4r)-7'-(5-Chloropyridin-3-yl)-4-methoxy-5"-methyl-3',4'-dihydrodispiro[cyclohexane-1,2'-naphthalene-1', 2"-imidazol]-4"-amine;

(1s,4s)-4-Methoxy-5"-methyl-7'-[5-(prop-1-yn-1-yl)pyridin-3-yl]-3',4'-dihydrodispiro[cyclohexane-1,2'-naphthalene-1',2"-imidazol]-4"-amine;

(1r,4s)-4-Methoxy-5"-methyl-7'-[5-(prop-1-yn-1-yl)pyridin-3-yl]-3',4'-dihydrodispiro[cyclohexane-1,2'-naphthalene-1',2"-imidazol]-4"-amine;

3-(4"-Amino-5"-methyl-3',4'-dihydrodispiro[cyclopropane-1,2'-naphthalene-1',2"-imidazol]-7'-yl)-5-chlorobenzonitrile ;

3-[(1r,4s)-4"-Amino-4-methoxy-5"-methyl-3',4'-dihydrodispiro[cyclohexane-1,2'-naphthalene-1',2"-imidazol]-7'-yl]-5-chlorobenzonitrile;

3-[(1s,4s-4"-Amino-4-methoxy-5"-methyl-3',4'-dihydrodispiro[cyclohexane-1,2'-naphthalene-1',2"-imidazol]-7'-yl]-5-chlorobenzonitrile;

3-[(1r,4s)-4"-Amino-4-methoxy-5"-methyl-3',4'-dihydrodispiro[cyclohexane-1,2'-naphthalene-1',2"-imidazol]-7'-yl]-5-chlorobenzonitrile, isomer 1; and 3-[(1r,4s)-4"-Amino-4-methoxy-5"-methyl-3',4'-dihydrodispiro[cyclohexane-1,2'-naphthalene-1',2"-imidazol]-7'-yl]-5-chlorobenzonitrile, isomer 2;

or a pharmaceutically acceptable salt of any foregoing compound.

14. The compound or pharmaceutically acceptable salt thereof according to claim 1, wherein said compound is selected from:

3-[(1r,4s)-4"-amino-4-methoxy-5"-methyl-3',4'-dihydrodispiro[cyclohexane-1,2'-naphthalene-1',2"-imidazol]-7'-yl]-5-chlorobenzonitrile:

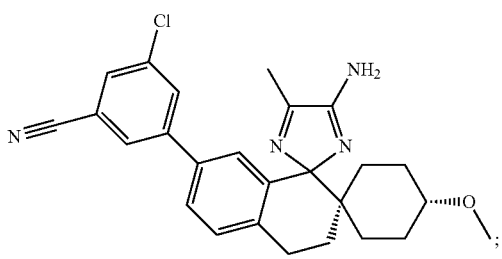

3-[(1r,4s)-4″-amino-4-methoxy-5″-methyl-3′,4′-dihydro-dispiro[cyclohexane-1,2′-naphthalene-1′,2″-imidazol]-7′-yl]-5-chlorobenzonitrile, isomer 1:

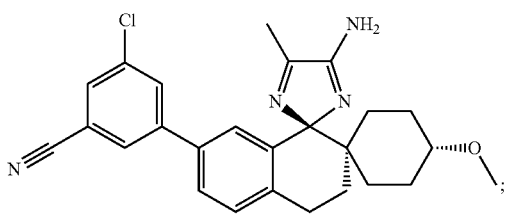 [SMILES: CO[C@H]1CC[C@@]2(CCc3ccc(-c4cc(Cl)cc(C#N)c4)cc3[C@@]23N=C(C)C(N)=N3)CC1]

and
3-[(1r,4s)-4″-amino-4-methoxy-5″-methyl-3′,4′-dihydro-dispiro[cyclohexane-1,2′-naphthalene-1′,2″-imidazol]-7′-yl]-5-chlorobenzonitrile, isomer 2:

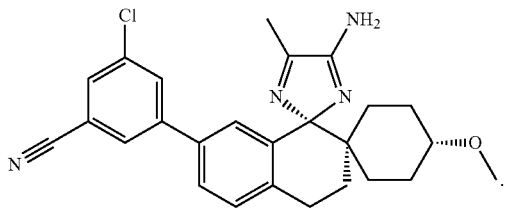 [SMILES: CO[C@H]1CC[C@@]2(CCc3ccc(-c4cc(Cl)cc(C#N)c4)cc3[C@]23N=C(C)C(N)=N3)CC1]

15. The compound or a pharmaceutically acceptable salt thereof according to claim 1, wherein said compound is (1r, 4s)-7′-(5-chloropyridin-3-yl)-4-methoxy-5″-methyl-3′,4′-dihydrodispiro[cyclohexane-1,2′-naphthalene-1′,2″-imidazol]-4″-amine:

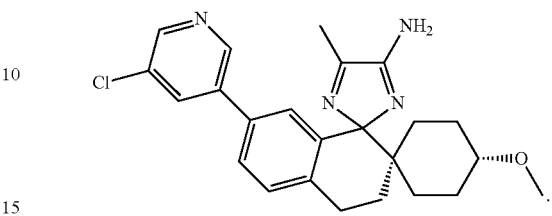

16. A pharmaceutical composition comprising as active ingredient a therapeutically effective amount of a compound according to any one of claim 1, 13, 14, or 15, or a pharmaceutically acceptable salt thereof, in association with at least one pharmaceutically acceptable excipient, carrier or diluent.

17. A method of treating Alzheimer's Disease in a patient in need thereof, comprising administering to said patient a therapeutically effective amount of a compound according to any one of claim 1, 13, 14 or 15, or a pharmaceutically acceptable salt thereof.

18. A method of treating an Aβ-related pathology in a patient in need thereof, comprising administering to said patient a therapeutically effective amount of a compound according to any one of claim 1, 13, 14 or 15, or a pharmaceutically acceptable salt thereof, and at least one cognitive enhancing agent, memory enhancing agent, or choline esterase inhibitor, wherein said Aβ-related pathology is Alzheimer's Disease.

* * * * *